(12) United States Patent
Heaton et al.

(10) Patent No.: US 7,555,792 B2
(45) Date of Patent: Jul. 7, 2009

(54) PATIENT COOLING ENCLOSURE

(75) Inventors: Keith Patrick Heaton, Parkstone Poole (GB); Christopher Guy Coward, Northmoor Park Wareham (GB); Mark Stephen James Beard, West Moors Ferndown (GB); Peter Charles Stacy, Ferndown (GB); David George Whyte, Wareham (GB)

(73) Assignee: KCI Licensing, Inc., San Antonio, TX (US)

( * ) Notice: Subject to any disclaimer, the term of this patent is extended or adjusted under 35 U.S.C. 154(b) by 365 days.

(21) Appl. No.: 11/518,136

(22) Filed: Sep. 8, 2006

(65) Prior Publication Data

US 2007/0073369 A1 Mar. 29, 2007

Related U.S. Application Data

(63) Continuation-in-part of application No. 11/154,321, filed on Jun. 16, 2005, which is a continuation-in-part of application No. 10/785,547, filed on Feb. 24, 2002, now Pat. No. 7,226,471, which is a continuation-in-part of application No. 10/290,938, filed on Nov. 8, 2002, now Pat. No. 6,945,987, application No. 11/518,136, which is a continuation-in-part of application No. 10/398,338, filed as application No. PCT/GB99/103688 on Nov. 5, 1999, now Pat. No. 6,942,687.

(51) Int. Cl.
*A61G 10/04* (2006.01)

(52) U.S. Cl. .................. 5/423; 5/284; 607/107

(58) Field of Classification Search .......... 5/713, 5/644, 941, 421, 423, 284; 607/107
See application file for complete search history.

(56) References Cited

U.S. PATENT DOCUMENTS

| 2,093,834 | A | * | 9/1937 | Gaugler ..................... 4/536 |
|---|---|---|---|---|
| 2,104,589 | A | | 1/1938 | Hartman |
| 2,603,214 | A | | 7/1952 | Taylor |
| 2,745,167 | A | | 5/1956 | Cross |
| 3,283,520 | A | | 11/1966 | Donohue et al. |
| 3,710,791 | A | | 1/1973 | Deaton |
| 3,909,858 | A | | 10/1975 | Ducker |
| 3,999,541 | A | | 12/1976 | Tabor |

(Continued)

FOREIGN PATENT DOCUMENTS

EP 0164086 A1 12/1985

(Continued)

OTHER PUBLICATIONS

PCT International Preliminary Report for PCT International Application PCT/US03/35134; Mar. 2, 2005.

(Continued)

*Primary Examiner*—Michael Trettel

(57) ABSTRACT

An apparatus to provide thermal control to a patient comprises a neck member having a surface defining at least one opening, the surface configured to be spaced apart from a neck area of the patient. The neck member includes an air inlet to receive cooled air from an air source. The at least one opening is in fluid communication with the air inlet to direct cooled air from the air source and toward the neck area of the patient to provide the thermal control to the patient.

3 Claims, 32 Drawing Sheets

U.S. PATENT DOCUMENTS

| | | | |
|---|---|---|---|
| 4,000,749 A | 1/1977 | Busco | |
| 4,170,998 A | 10/1979 | Sauder | |
| 4,237,914 A | 12/1980 | Gantz | |
| 4,506,511 A | 3/1985 | Cameto et al. | |
| 4,572,188 A | 2/1986 | Augustine et al. | |
| 4,638,519 A | 1/1987 | Hess | |
| 4,660,388 A | 4/1987 | Greene, Jr. | |
| 5,044,364 A * | 9/1991 | Crowther | 607/107 |
| 5,081,339 A | 1/1992 | Stine | |
| 5,097,548 A | 3/1992 | Heck et al. | |
| 5,168,589 A | 12/1992 | Stroh et al. | |
| 5,331,991 A | 7/1994 | Nilsson | |
| 5,350,417 A | 9/1994 | Augustine | |
| 5,405,370 A | 4/1995 | Feraidoon | |
| 5,443,488 A * | 8/1995 | Namenye et al. | 607/104 |
| 5,658,325 A | 8/1997 | Augustine | |
| 5,699,570 A | 12/1997 | Wilkinson et al. | |
| 5,749,109 A | 5/1998 | Kappel | |
| 5,815,864 A | 10/1998 | Sloop | |
| 5,817,147 A | 10/1998 | Wolf | |
| 5,832,919 A | 11/1998 | Kano et al. | |
| 5,928,273 A | 7/1999 | Schmidt | |
| 6,210,427 B1 | 4/2001 | Augustine et al. | |
| 6,210,428 B1 | 4/2001 | Augustine et al. | |
| 6,282,737 B1 | 9/2001 | Vrzalik | |
| 6,487,871 B1 * | 12/2002 | Augustine et al. | 62/259.3 |
| 6,689,155 B2 * | 2/2004 | Gammons et al. | 607/109 |
| 6,730,115 B1 | 5/2004 | Heaton | |
| 6,764,502 B2 | 7/2004 | Bieberich | 607/104 |
| 6,855,158 B2 * | 2/2005 | Stolpmann | 607/108 |
| 7,226,471 B2 * | 6/2007 | Heaton et al. | 607/104 |
| 2002/0058975 A1 * | 5/2002 | Bieberich | 607/104 |
| 2004/0050411 A1 | 3/2004 | Lawrence | |
| 2005/0283913 A1 | 12/2005 | Heaton et al. | 607/104 |

FOREIGN PATENT DOCUMENTS

| | | |
|---|---|---|
| FR | 2754167 | 4/1998 |
| GB | 2263872 A | 8/1993 |
| WO | WO 95/10211 | 4/1995 |
| WO | WO 97/36521 | 10/1997 |
| WO | WO 97/42919 | 11/1997 |
| WO | WO 01/50988 A1 | 7/2001 |

OTHER PUBLICATIONS

International Search Report and Written Opinion issued in International Application No. PCT/US07/77878, mailed Oct. 9, 2008.

* cited by examiner

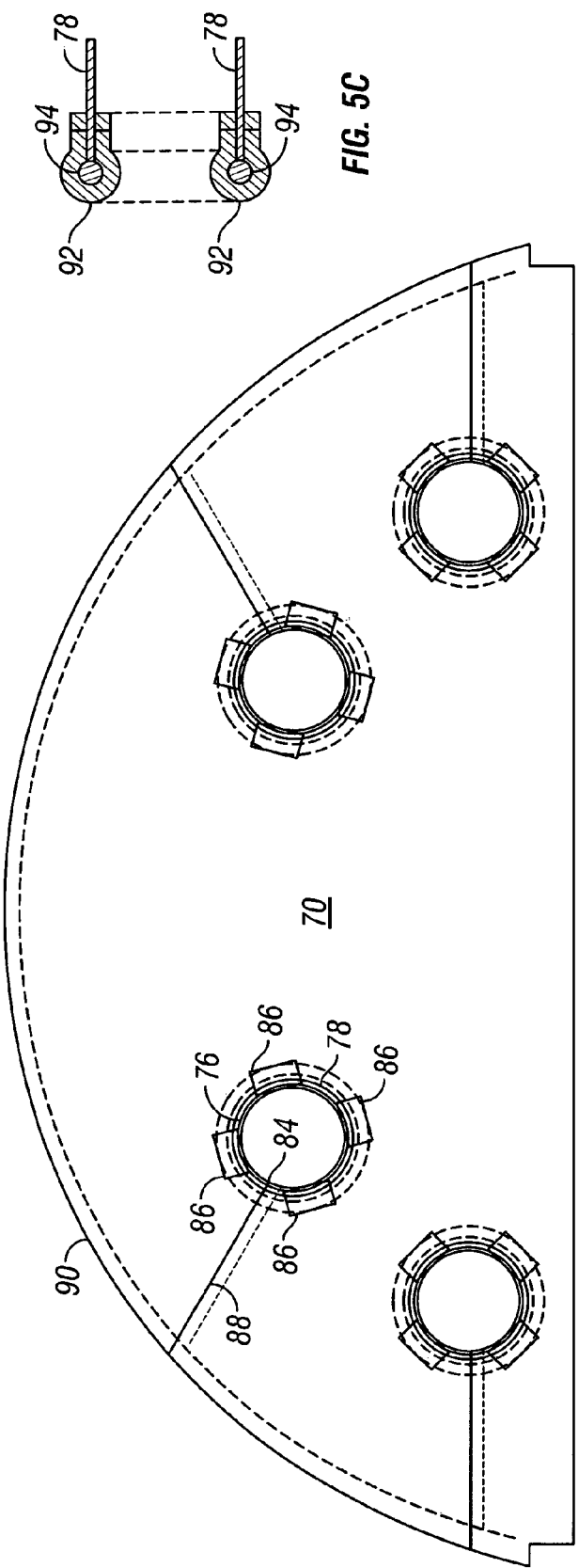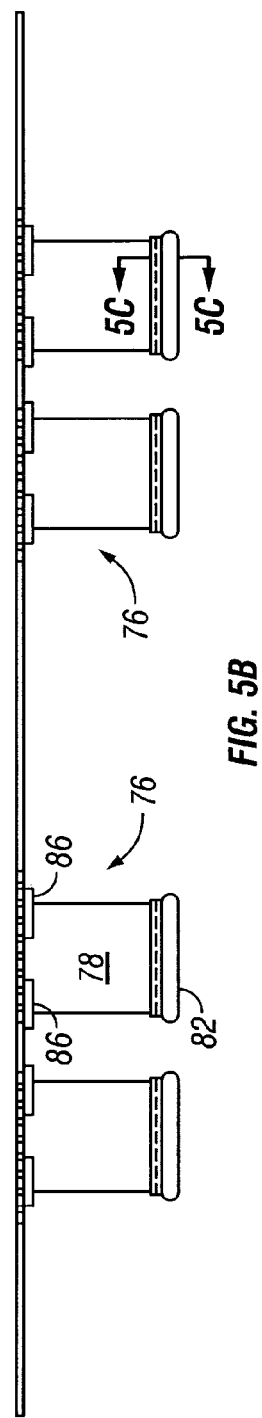
FIG. 5A
FIG. 5B
FIG. 5C

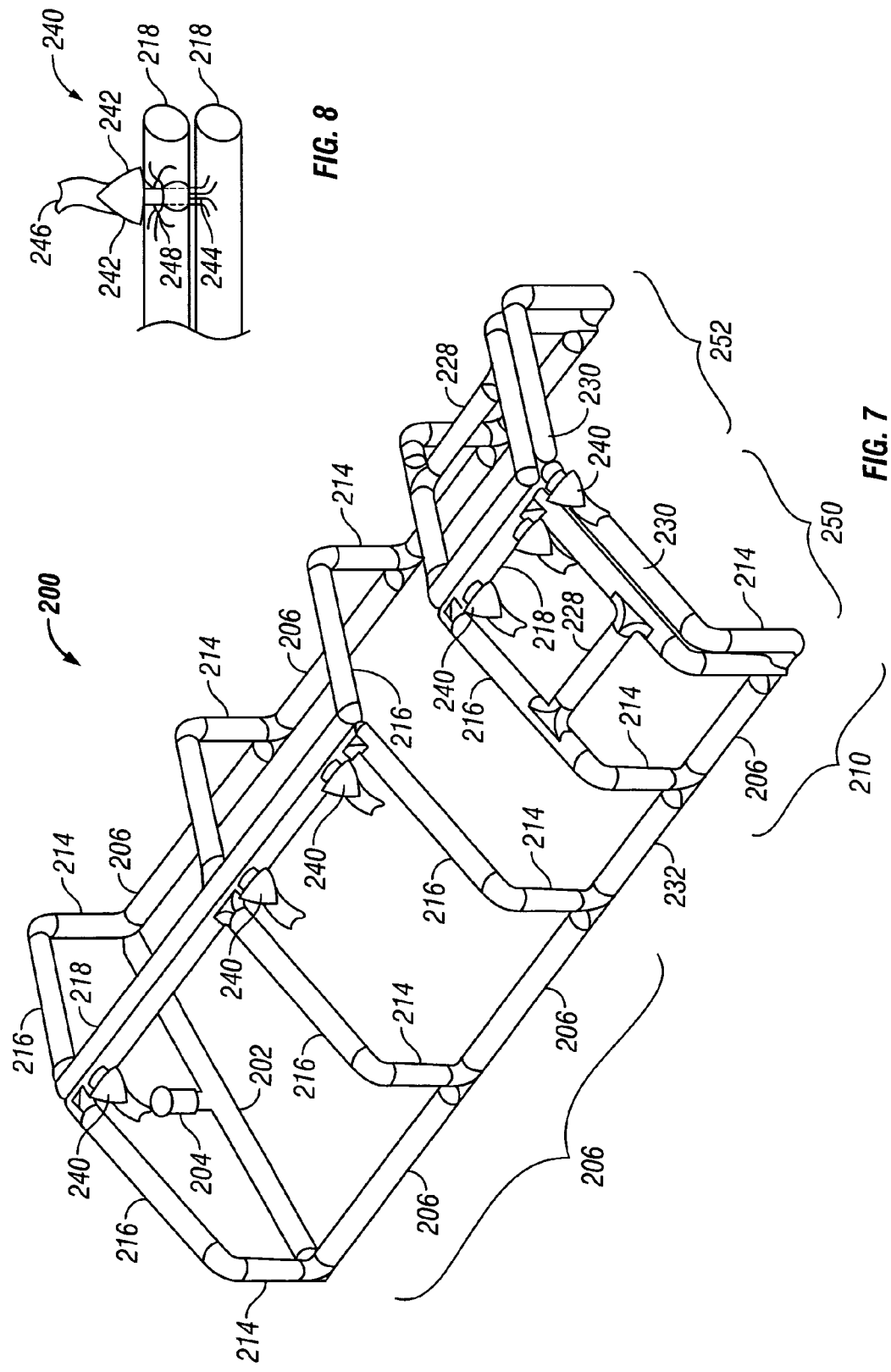

PATIENT COOLING ENCLOSURE

RELATED APPLICATIONS

This application is a continuation-in-part of co-pending U.S. patent application Ser. No. 11/1154,321, entitled "Patient Cooling System," filed on Jun. 16, 2005, and still pending, which is a continuation-in-part of U.S. patent application Ser. No. 10/785,547, entitled "Patient Cooling System," filed on Feb. 24, 2004, now U.S. Pat. No. 7,226,471, which is a continuation in part of U.S. patent application Ser. No. 10/290,938, entitled "Patient Cooling System," filed on Nov. 8, 2002, now U.S. Pat. No. 6,945,987. This application is also a continuation-in-part of U.S. patent application Ser. No. 10/398,338, entitled "Patient Cooling Enclosure," filed on Mar. 25, 2003, now U.S. Pat. No. 6,942,687 which claims priority to international application number PCT/GB/99103688, filed on Nov. 5, 1999, which claims priority to United Kingdom application number GB9824431, filed on Nov. 6, 1998. The foregoing U.S. applications are incorporated herein by reference, and all are claimed as priority to the present application.

FIELD OF THE INVENTION

This invention relates generally to systems for cooling a person for therapeutic purposes. More particularly, this invention relates to an enclosure or tent and support system for a patient who is to be cooled to a temperature below normal body temperature, or heated.

BACKGROUND

International patent applications published under WO 97/42919 and WO 00/27323, which are incorporated herein by reference for all purposes, describe systems for rapidly cooling a patient to a temperature a few degrees below normal blood temperature, e.g. in the range of about 32 to 34 degrees Celsius. This clinical procedure has been used with some success in reducing brain damage to cardiac or stroke patients.

SUMMARY OF THE INVENTION

The present disclosure provides an improved patient cooling system, which, according to a first feature of the invention, comprises an enclosure or tent having an inlet connected to an air cooling system, and an outlet which is connected to re-circulate exhaust air back to the inlet of the cooling system in order to minimize energy losses. Preferably, the enclosure is arranged so that it can be used on a variety of patient support devices such as mattresses, including support devices mounted in an ambulance fitted with a suitable source of cold air.

Preferably, the enclosure is connected to a cooling system that includes an inlet for ambient air, a main blower that supplies air to the enclosure via the cooling section of a refrigeration system, and a re-circulation duct that connects an outlet from the air tent to the inlet side of the main blower.

Preferably, the patient is supported on a mattress system comprising a plurality of inflatable compartments, which can also be supplied with cooled air. Preferably, the compartments comprise elongate members that extend transversely across the width of the mattress, and can be alternately inflated to avoid any particular regions of the patient's body from being subjected to high pressure continuously.

According to a further feature of the invention, there is provided a patient support mattress comprising a plurality of transversely extending inflatable compartments, which are so arranged that each compartment can be alternately pressurized, either with relatively low pressure cold air, which assists in cooling the patient but provides relatively little support, or with higher pressure air which acts to support the patient, but provides relatively less cooling effect.

According to a still further feature of the invention there is provided an air tent or enclosure for enclosing a patient in a controlled environment, comprising a plurality of panels of flexible material, and having an opening with releasable fastener means to enable a patient to be enclosed, at least one panel including an aperture or apertures to allow the passage of a duct or pipe to communicate with the interior of the enclosure, the aperture comprising a radially collapsible sleeved opening having a split along the side of the sleeve which communicates with a further split in the panel for introduction of the conduit, the sleeve being flexible and being adapted to be tightened around the conduit.

Preferably the outer edge of the sleeve is provided with a ring of hook or loop covered attachment material, which is adapted to cooperate with inter-engageable loop or hook material on the panel around the base of the sleeve, whereby the sleeve can be secured tightly around the conduit after it has been placed in position, by twisting the sleeve around the conduit and pressing the ring of material against the co-operating material on the panel.

The present disclosure encompasses several different embodiments of air tents. Some embodiments have tents that fully enclose the patient. Other embodiments have tents that allow the patient's head to protrude from the enclosure. In one embodiment, the air tent is supported by the internal air pressure of the tent. In another embodiment, the tent is supported by a framework of tent poles or equivalent structural support members. In yet another and currently preferred embodiment, the tent is supported by a framework of inflatable, collapsible tubes. In both the rod framework and the inflatable tube framework, the framework is preferably bifurcated along a line parallel to the longitudinal axis of the air tent, to enable the tent to be split open along the line of bifurcation. The framework is also preferably transversely split into two or more sections to enable the tent to flex with the articulation of a hospital bed frame.

According to another feature of the present disclosure, a central air flow system is integrally incorporated within the mattress, and connected to a thermal control unit ("TCU"). In this manner, air is cooled and dehumidified in the TCU. Next, it is transferred between the TCU and a central manifold system via one or more interface units, which may be configured in multiple orientations and are adapted to be universally connected to air-flow system in 180 degree orientations should circumstances require.

Next, depending on the therapy cycle, air-flow is diverted through the central manifold system to one of two circuits by a flow valve. The first circuit allows air to pass through the central manifold and to one of two outer channels to the mattress air cells, and then back through the opposite central manifold. Return flow from the first circuit merges with second circuit air-flow in an outlet duct, which allows the air to be transferred back to the TCU via the interface unit for cooling/heating and dehumidification.

The second circuit allows air to be directed to the vent hose or vents through a central channel, which allows the air to flow through the vent hose and onto the patient's neck to thermally cool or heat the patient. The air then flows through the tent enclosure to the foot end of the mattress, where air is pulled into the re-circulation duct. The return flow merges with first-circuit air-flow in the outlet duct in a similar fashion as described above.

According to another feature of the present disclosure, a neck member is incorporated into the central air flow system and the TCU. The neck member includes surfaces that define openings through which warm or cool air can flow. The openings are positioned such that the warm or cool air is directed around the neck area of the patient to provide thermal control to the patient.

These and other aspects and features of the present disclosure will be readily apparent to those skilled in the art from the following detailed description taken in conjunction with the annexed sheets of drawings, which illustrate the invention.

BRIEF DESCRIPTION OF THE DRAWINGS

FIG. 5A is an enlarged view of the end panel of FIG. 4C.

FIG. 5B is a plan view of the end panel of FIG. 5A.

FIG. 5C is a detailed view of a cross-section through part of the structure of FIG. 5A.

FIG. 7 is a perspective view of one embodiment of a patient enclosure support framework of inflatable tubes.

FIG. 8 is a three-dimensional view of an inflatable connection means for removably connecting parts of the framework together.

DETAILED DESCRIPTION

Based on the description and illustrations provided herein, the many benefits provided by the invented structure and methods of utilization are apparent. These described benefits, as well as those that are inherent to those skilled in the art, fall within the scope of the invention of the present patent application as limited only by the claims appended hereto.

Figure 1A:
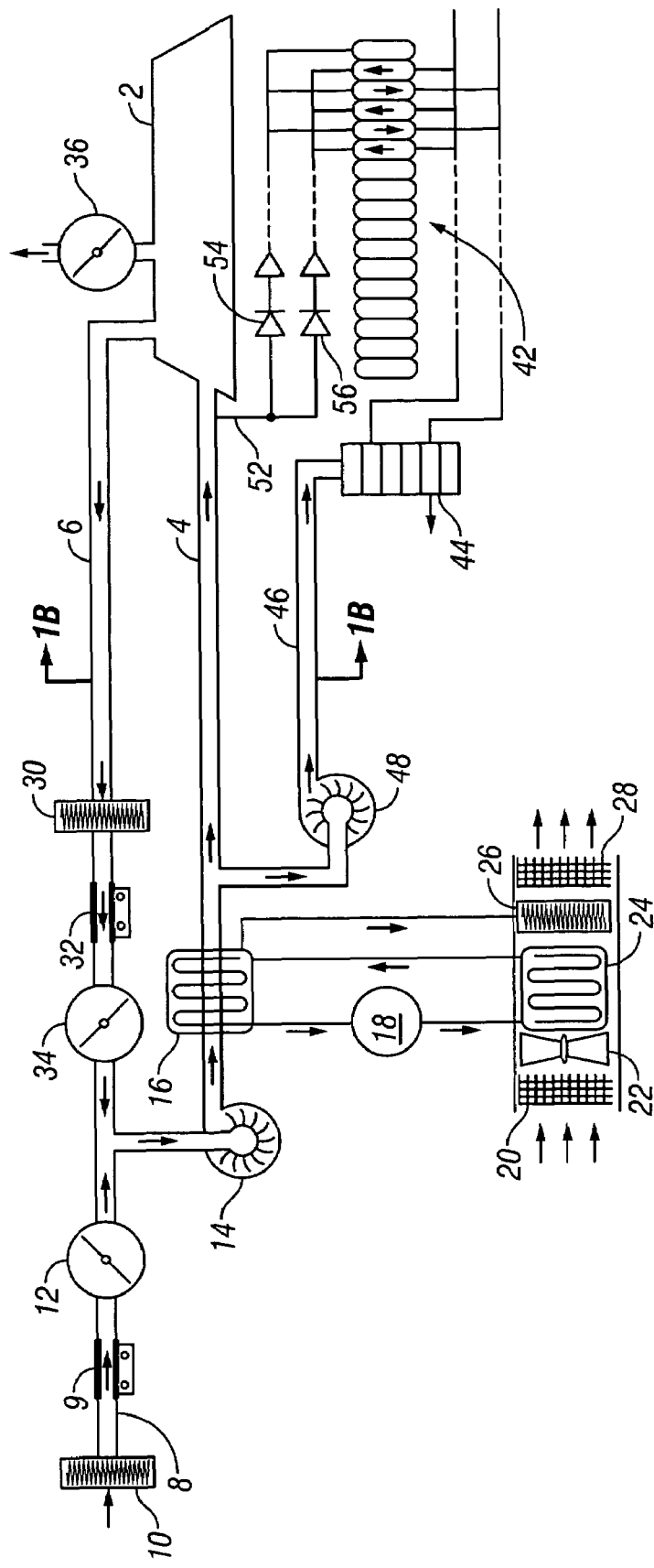
FIG. 1A is a schematic diagram of a patient cooling system according to the invention.

Referring to the drawings, FIG. 1A illustrates the general layout of a patient cooling system in accordance with the invention, comprising an air tent 2 forming an enclosure with a tent inlet duct 4 and a tent outlet duct 6. The air tent 2 is preferably constructed from panels of fabric material, as described in more detail below.

The air tent 2 is supplied with cool air through an air inlet duct 8, with a system intake filter 10, an intake flow sensor 9, and an intake valve 12 comprising a movable vane that communicates with a main blower 14. This pressurizes the air, and it then is passed through a heat exchanger 16, which comprises the evaporator section of a refrigeration circuit. The refrigeration circuit further comprises a compressor 18 and a condenser 24, which is provided in a conventional fashion with a condenser fan 22 having a condenser intake filter 20, a wick 26 for absorbing condensate drain from the evaporator section, and an outlet air filter 28.

Having passed through the heat exchanger 16 and thus being cooled, the air passes into the enclosure of the air tent 2 via the tent inlet duct 4, circulates past the patient, and leaves the enclosure via the tent outlet duct 6. The outlet duct 6 is connected by means of a re-circulation filter 30 to a re-circulation flow sensor 32 and a re-circulation valve 34 comprising a vane that can be moved in order to control the proportion of re-circulated air.

The air tent 2 is also provided with a vane type exhaust valve 36 that enables the pressure inside the air tent 2 to be independently controlled. In this way, the proportion of recirculated air and the internal temperature of the air tent 2 can be controlled without unduly increasing or decreasing the total pressure inside the enclosure.

Figure 1B:
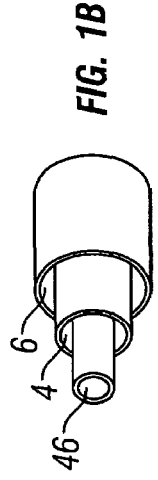
FIG. 1B is a partial cross-section view of the coaxial hose set according to the invention.

The apparatus also includes a patient-supporting mattress, indicated generally at 42 in FIG. 1A, which comprises a plurality of inflatable compartments or cells to which air is supplied through an arrangement of servo valves 44 which are connected to the cooling circuit by a conduit 46 containing a further blower 48. As illustrated in FIG. 1A and FIG. 1B, the conduit 46 is incorporated in a coaxial hose set, forming a central core thereof, so that the air passing through the conduit 46 is insulated from the ambient temperature by the outer coaxial passageways of the hose set that comprise tent inlet duct 4 and tent outlet duct 6.

Figure 2:
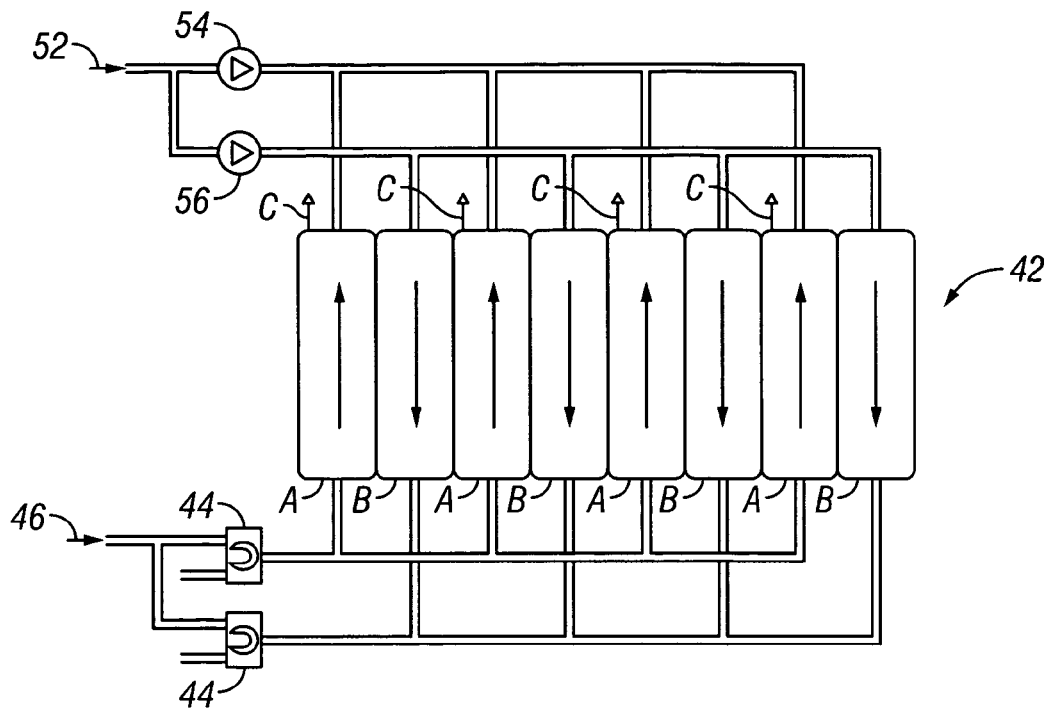
FIG. 2 is a schematic diagram of a patient support mattress having an air flow control system.

FIG. 2 illustrates in more detail how air is supplied to the mattress 42, so that alternate cells are pressurized with high and low pressure air in successive cycles. As shown, there are two interleaved sets of cells or compartments A and B, both of which are connected continuously to a source of cold air at low pressure by means of valves 54 and 56 respectively. In the general arrangement of FIG. 1A, these will normally be connected via line 52 to the tent inlet duct 4 which supplies the air tent 2, and will therefore provide little supporting effect for the patient (being at low pressure) but will have fairly substantial cooling capacity.

The high pressure air supply through conduit 46 driven by the blower 48 (as described above with reference to FIG. 1A) is connected to each set of cells A or B, by a respective servo valve 44, and these are activated alternately so that during a first cycle, all cells A are inflated to a high pressure so as to support the patient while cells B are connected to the tent outlet duct 6 for re-circulation. A controlled amount of leakage is of course permitted through the fabric of each cell, as indicated by arrow C, since the high pressure air cannot escape via the non-return valves 54, 56 (as shown in FIG. 1A and FIG. 2). Since the high pressure air supply via conduit 46 has been subjected to greater pressurization, it is, of course, at a somewhat higher temperature than the low pressure supply, and thus, primarily performs a supporting function rather than a cooling function for the patient's body.

At the same time, however, the cells B are receiving the supply of colder air via line 52 at relatively low pressure, so these cells primarily provide a cooling function rather than a supporting function.

At the next cycle, the high pressure air supply is shut off from the cells A, by operating their respective servo valve 44 and instead, they are connected to the tent outlet duct 6 for re-circulation so that they now act primarily to provide cooling, as passageways for the cold air supply via line 52. At the same time, the cells B are connected to the high pressure supply, so as to take over the patient supporting function, in the same way, as described above for the cells A in the previous cycle.

In this way, each region of the patient's body is alternately supported by the high pressure, or subjected to cooling, rather than being continuously subjected to high pressure.

FIGS. 3A-3D illustrate one embodiment of an air tent 2. As shown, the air tent comprises a generally semi-cylindrical fabric structure, having a base portion (not visible in the Figure) that is supported on a mattress cover 62 enclosing a mattress structure of the kind described above with reference to FIG. 2. Although the semi-cylindrical shape is beneficial and advantageous, other tent shapes are also suitable and should be understood to fall within the scope of the claims, unless otherwise specified.

Figure 3A:
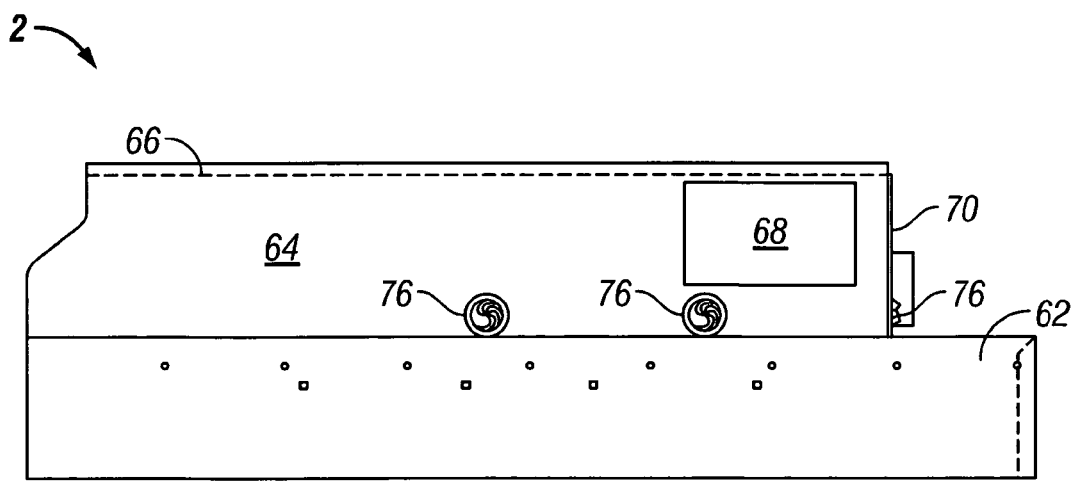
FIG. 3A is a side elevation of one embodiment of a patient enclosure.
Figure 3B:
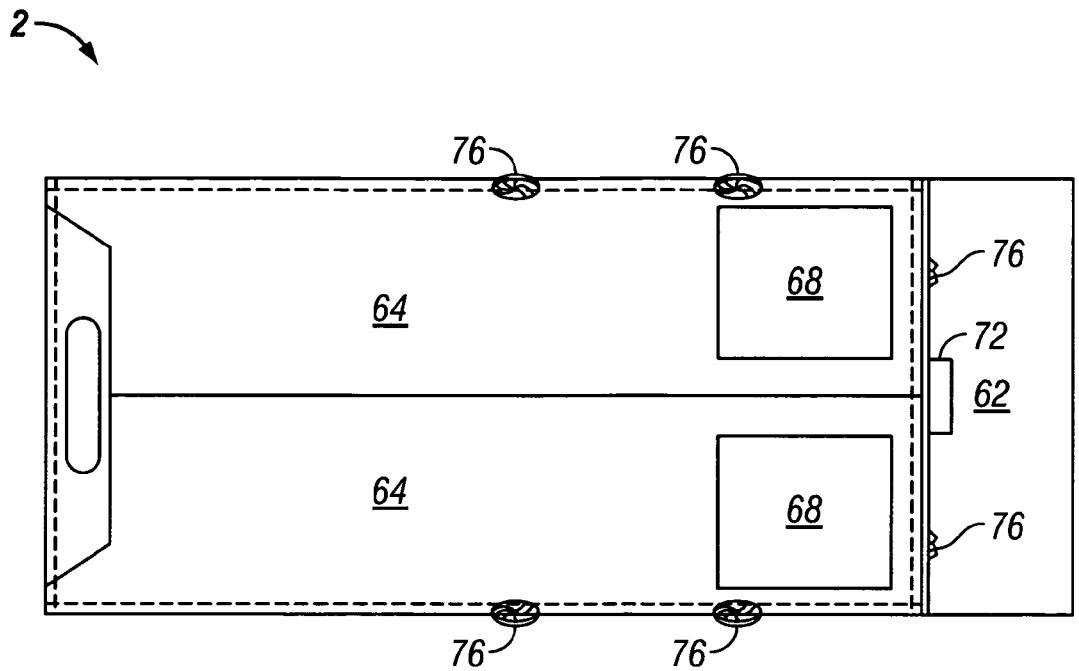
FIG. 3B is a plan view of the patient enclosure of FIG. 3A.
Figure 3C:
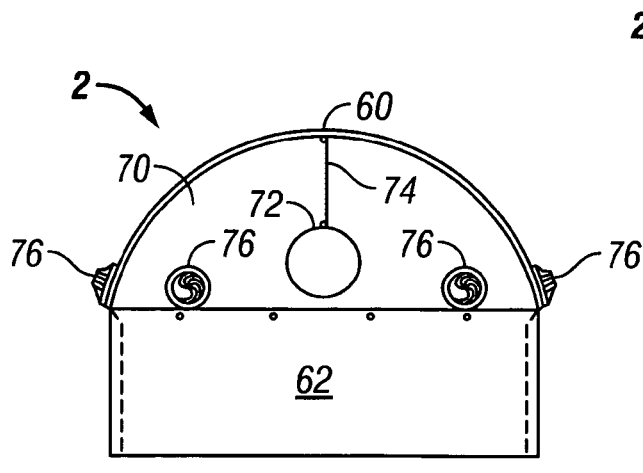
FIG. 3C is an end elevation of the enclosure of FIG. 3A.
Figure 3D:
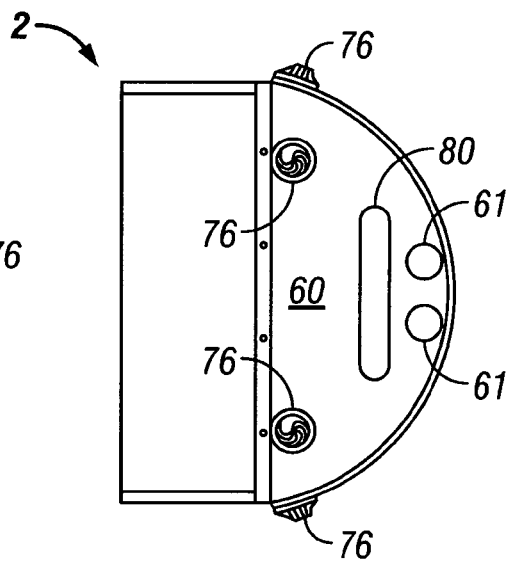
FIG. 3D is an end elevation of the enclosure of FIG. 3A, opposite of the end elevation shown in FIG. 3C.

As can be seen from the plan view of FIG. 3B, the upper or covering portion of the enclosure comprises a pair of elongate flaps 64 whose adjoining edges can be connected with a Velcro.® type seal (i.e., separable complementary hook and loop fasteners) or similar seal 66, each flap being formed with a flexible, transparent inspection panel 68. A head end panel 70 (FIG. 3C) is formed with an aperture 72 for the neck of the patient, to allow the patient's head to protrude from the enclosure, and this aperture 72 is connected to the circular edge of the head end panel 70, by means of a slit 74 to facilitate the process of positioning the patient's neck. This slit is also provided with a Velcro type or similar seal 66 along its adjacent edges, for subsequent closure.

The air tent 2 is also provided with a series of specially adapted apertures 76, for the entry of various conduits and connectors, as will be described in more detail below, while the foot end 60 (FIG. 3D) is provided with a pair of air input ports 61 for air input ducts, as well as a re-circulation aperture 80 for connection to re-circulation and pressure relief valves.

Figure 4A:
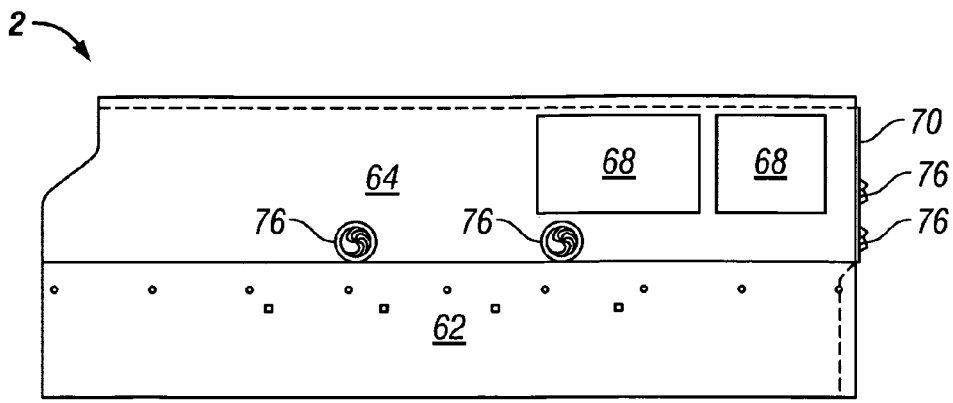
FIG. 4A is a side elevation of another embodiment of a patient enclosure.
Figure 4B:
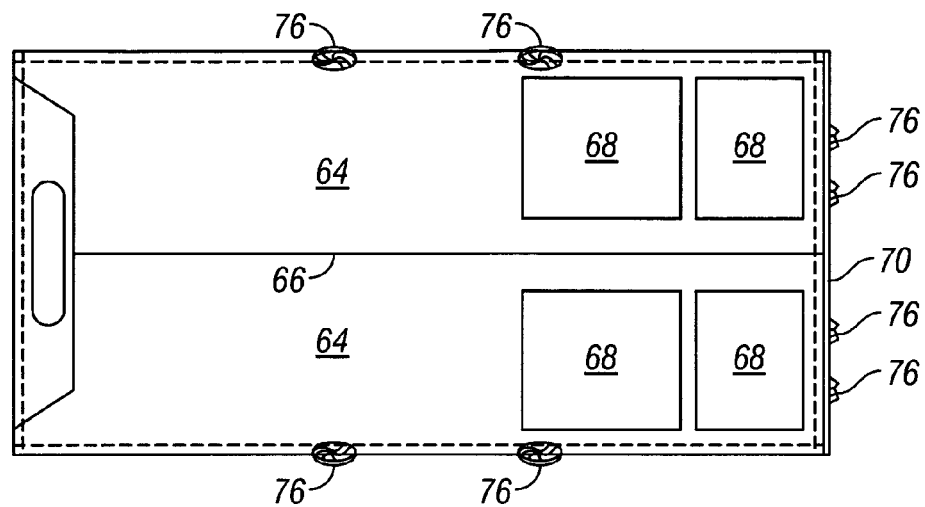
FIG. 4B is a plan view of the enclosure of FIG. 4A.
Figure 4C:
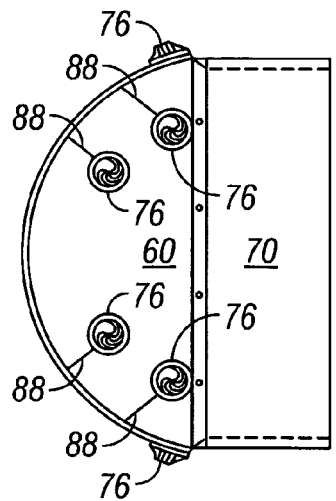
FIG. 4C is an end elevation of the enclosure of FIG. 4A.

FIGS. 4A, 4B, and 4C illustrate a "full enclosure" version of the air tent 2 of FIGS. 3A, 3B, 3C, and 3D, in which, as depicted in FIGS. 4A and 4B, the enclosure is longer so as to enclose the patient's head. This version includes additional transparent inspection panels 68 in the head region to allow the patient external vision. In this case, of course, the head end panel 70 does not include a neck aperture.

In the embodiments depicted in FIGS. 3A-3D and 4A-C, the air tent 2 is supported by its internal air pressure, which is maintained by air supplied through the tent inlet duct 4. In alternative embodiments described further below, poles, rods, beams, inflatable air tubes, or equivalent support structures are used to support the air tent 2.

FIGS. 5A and 5B illustrate the arrangement by which pipes and conduits are passed through the walls of the air tent 2, with minimum air leakage. Each conduit aperture 76 is provided with a radially collapsible tubular sleeve 78 made of flexible material such as fabric. The tubular sleeve 78 is stitched into the head end panel 70 in the arrangement shown in FIG. 5A and projects from the wall as shown in FIG. 5B. The outer edge of the tubular sleeve 78 is reinforced with a split aluminum anchor ring 92 (FIG. 5C) having a covering of Velcro type material 94 stitched around it. Thus the Velcro-covered ring shown in FIG. 5B forms a reinforced sleeve rim 82 at the outer end of the tube to maintain the tubular sleeve 78 in a generally circular configuration as it is closed around the conduit. This reinforced sleeve rim 82, as well as the tubular sleeve 78 itself, is formed with corresponding splits 84 which enable the tubular sleeve to be closed around a conduit, as explained in more detail below.

Continuing in FIG. 5A, four Velcro type "loop" pads 86 stitched to the head end panel 70 of the air tent 2 surround the tubular sleeve 78. The panel itself includes a slit 88 that extends from the spilt 84 of the tubular sleeve 78 to the outer edge 90 of the panel. In this way, a pipe or conduit (which may for example already be connected to the patient) can be passed into the enclosure, so as to exit through the sleeve 78, without disconnecting either end.

After the conduit has been properly positioned, the reinforced sleeve rim 82 is twisted around and squeezed into engagement with the conduit (not shown in the Figure), and pressed against the Velcro type pads 86. The rim 82 is then attached to the pads, locating the conduit tightly in position. It will be appreciated that this closure system works equally well for a wide range of conduit sizes. In addition, if any particular aperture 76 is not needed, the sleeve 78 can be twisted up more tightly to close the aperture completely (as indicated schematically in FIGS. 3A, 3B, 3C, 3D and FIGS. 4A, 4B, and 4C).

It will be appreciated that the slit 88 (shown in FIG. 5A) is also provided with suitable Velcro type or similar closure means along its adjacent edges, so that the entire closure can be made substantially leak proof, thus reducing significantly the overall re-circulation losses in the system.

Figure 6:
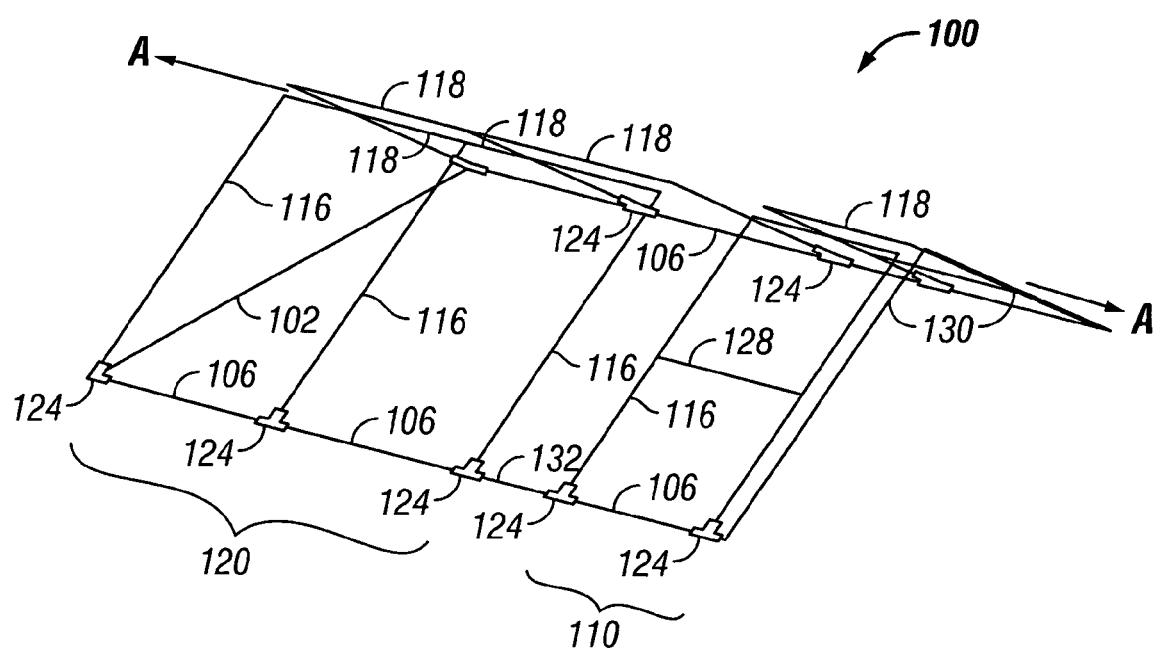
FIG. 6 is a perspective view of one embodiment of a patient enclosure support framework of trusses or rods.

As noted above, in some embodiments, the air tent 2 is supported by its internal air pressure. In an alternative embodiment, however, the air tent 2 is supported by a framework. FIG. 6 depicts a triangle-shaped embodiment of a support framework 100 for an air tent 2, although it will be understood that frameworks with more spacious dimensions may be preferable. The support framework 100 comprises a plurality of poles, rods, braces, or equivalent structural support members to raise and maintain the elongate flaps 64 (FIG. 4B) of the covering portion of the tent 2 above the patient. More particularly, the framework 100 comprises several base members 106, link members 132, rafter members 116, ridge members 118, purlin members 128, and a cross member 102.

Preferably, the framework 100 is at least partially, if not entirely, split along its longitudinal dimension A-A, and the rafter members 116 connected to the base members 106 through pivot joints 124 (or, in the alternative, through separable joints). In this manner, one or more of the split portions of the framework 100 may be pivoted away (or, if separable joints are used, removed altogether) to provide access to the patient. In yet further embodiments, the framework 100 is also split along its transverse dimension into two or more sections to facilitate articulation of the air tent 100 on an articulating bed frame. FIG. 6 shows a division in the framework 100 between an upper body section 110, a lower body section 120, and a head opening frame section 130. In this manner, the upper body section 110 and lower body section 120 can be positioned at angles with respect to each other that correspond with the articulating sections of an articulating bed frame.

FIG. 7 depicts another embodiment of a tubular support framework 200 for an air tent 2. This tubular support framework 200 comprises a plurality of inflatable tubes to support the elongate flaps 64 (FIG. 4B) of the covering portion of the tent 2 above the patient. More particularly, the framework 200 comprises several pneumatically connected feeder tubes 206, link tubes 232, vertical support tubes 214, rafter tubes 216, ridge tubes 218, purlin tubes 228, and a cross tube 202. Preferably, the tubular support framework 200 is provided with a high-pressure inflation source. The tubular support framework 200 may be supplied with air by connection of the air inlet port 204 with the air supply conduit 46 (FIG. 2), mediated through an independent servo valve or through the bank of servo valves 44 (FIG. 2) that supply air to the individual cells of the patient supporting mattress 42 (FIG. 2).

Preferably, the framework 200 is at least partially, if not entirely, split along its longitudinal dimension, between left and right halves 250 and 252, so that one or more of the split portions of the framework 200 may be pivoted away to provide access to the patient. In yet further embodiments, the framework 200 is also split along its transverse dimension into two or more sections to facilitate selective access to the patient and articulation of the air tent 200 on an articulating bed frame. In FIG. 7, the framework 200 is divided between an upper body section 210, a lower body section 220, and a head opening frame section 230. Either half of the upper body section 210 can be pivoted away from the patient to provide access to the upper body of the patient. Likewise, either half of the lower body section 220 can be pivoted away from the patient to provide access to the lower body of the patient.

FIG. 8 is a three-dimensional view of an inflatable quick-connect and quick-release closure means for releasably connecting parts of the framework 200, such as the ridge tubes 218 of the left and right halves of the framework 200, together. An inflatable tube connector 240 protrudes out of a ridge tube 218 on the left or right side 250 or 252 of the framework 200. The ridge tube 218 on the opposite side of the framework 200 has a hole 248 for receiving the inflatable tube connector 240. The tube connector 240 comprises a stem 244, a protuberance 242, and a pull tab 246 for pulling the connector 240 through hole 248. When inflated, the protuberance expands so that the diameter of its outer dimension exceeds the diameter of the hole 248, thereby resisting disconnection. As shown in FIG. 7, several connectors 240 are provided to close the left and right sides 250 and 252 of the framework 200.

The connector 240 can easily be removed from the corresponding hole 248 by pulling it out. Removal is even easier if the framework (which includes the connectors themselves) is first deflated. The stem 244 and protuberance 242 of the connector 240 are preferably inflatable, but in alternative embodiments may be filled with foam, cushioning material, or other compressible substances.

In operation, the air tent 2 is inflated by supplying high-pressure air to the tubular support framework 200. To gain access to the patient, it is contemplated that a caregiver will operate a user interface (such as a switch or computer input command) to turn off the air supply or a valve to deflate the framework 200. Upon deflation, the framework 200 becomes flexible and can easily be folded into an open position and out of the way. Alternatively, the caregiver may leave the tubular support framework inflated. Because the tubes are preferably constructed of flexible fabric or plastic material, they can easily be folded down while inflated.

Figure 9:
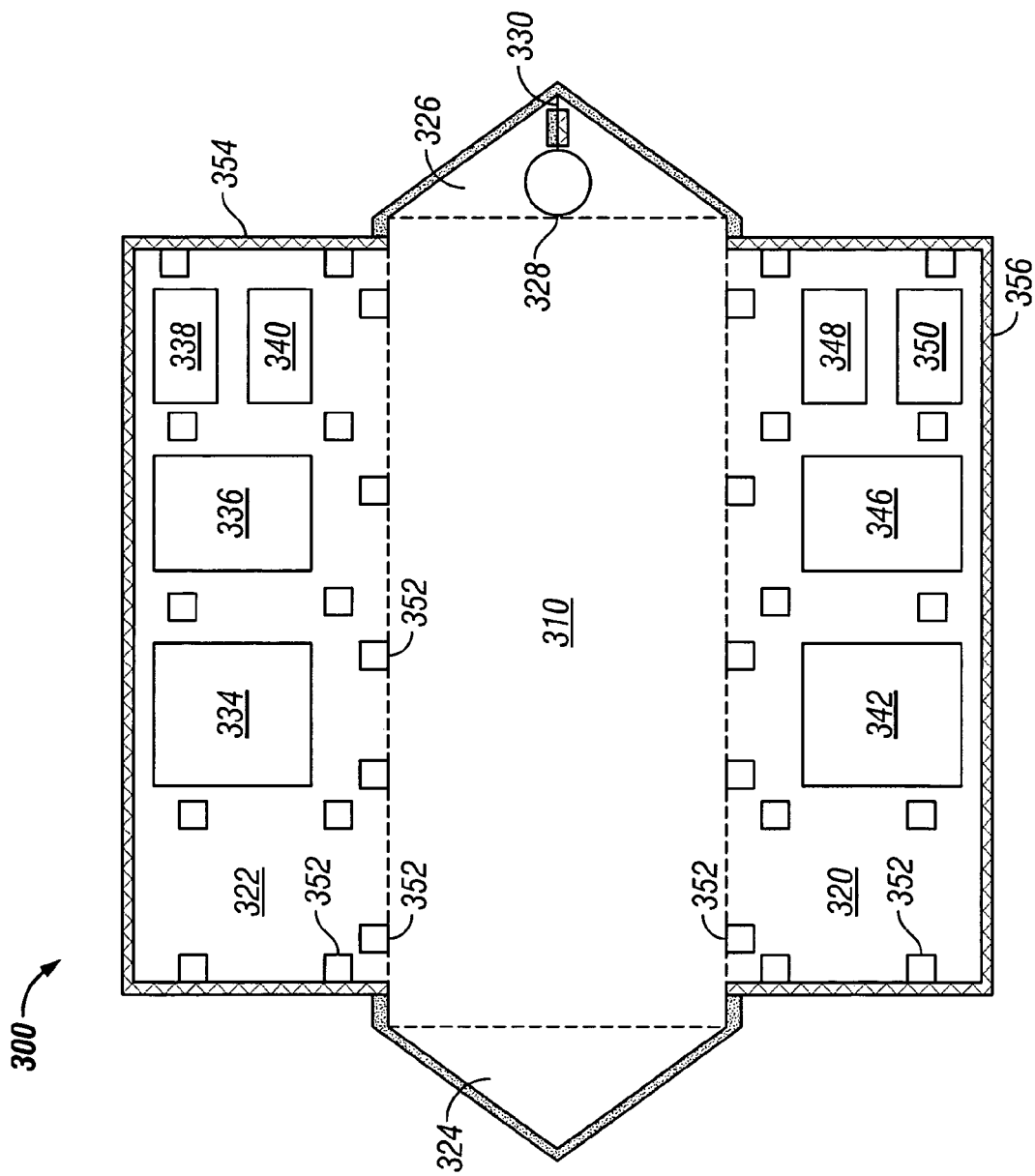
FIG. 9 depicts a layout of one embodiment of a tent designed to cover the patient enclosure framework of FIG. 7.

FIG. 9 depicts a layout of one embodiment of a tent 300 designed to cover the patient enclosure framework of FIG. 7. Tent 300 comprises a bottom sheet 310, a left side 320, a right side 322, a foot drape 324, and a head drape 326. The head drape 326 provides an opening 328 for a patient's head. The head drape 326 also provides a slit 330 that facilitates adjustment of the size of the head opening 328 and placement and removal of the patient and care lines to the patient. Other slits and flaps (not shown) may also be provided in the left side 320, right side 322, and foot drape 324 to facilitate insertion or removal of patient care lines, air supply hoses, and the like.

Clear plastic translucent windows 334, 336, 338, 340, 342, 346, 348, and 350 enable caregivers to see the patient and the patient to see his or her caregivers. A plurality of tube attachment connectors 352 are provided to attach the tent 300 to the tubular support framework 200. Although not shown in FIG. 9, tent 300 may be equipped with many of the same features shown in connection with FIGS. 3A-5C, including but not limited to air input ports 61, conduit apertures 76, and a recirculation aperture 80.

In one embodiment, the tent is also provided with a plurality of Velcro-type loop fasteners 354 and Velcro-type hook fasteners 356 to facilitate a better air seal. In an alternative embodiment, a sufficient number of quick-release connectors 240 (FIG. 7) are used and a sufficient volume of cool air is pumped into the tent to eliminate the need for Velcro-type fasteners.

Figure 10:
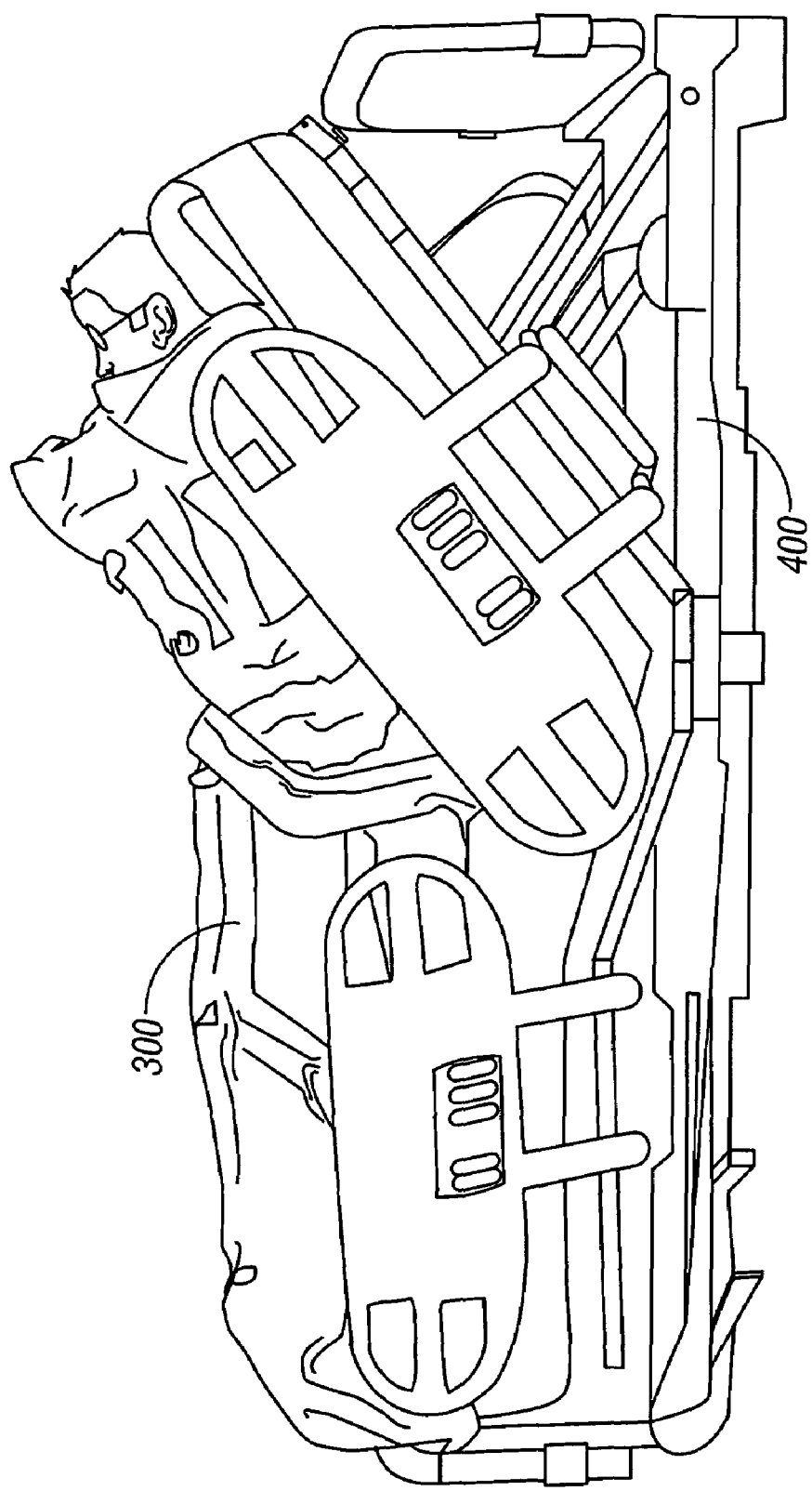
FIG. 10 is a perspective view of an embodiment of a patient support enclosure mounted on an articulating hospital bed frame.
Figure 11:
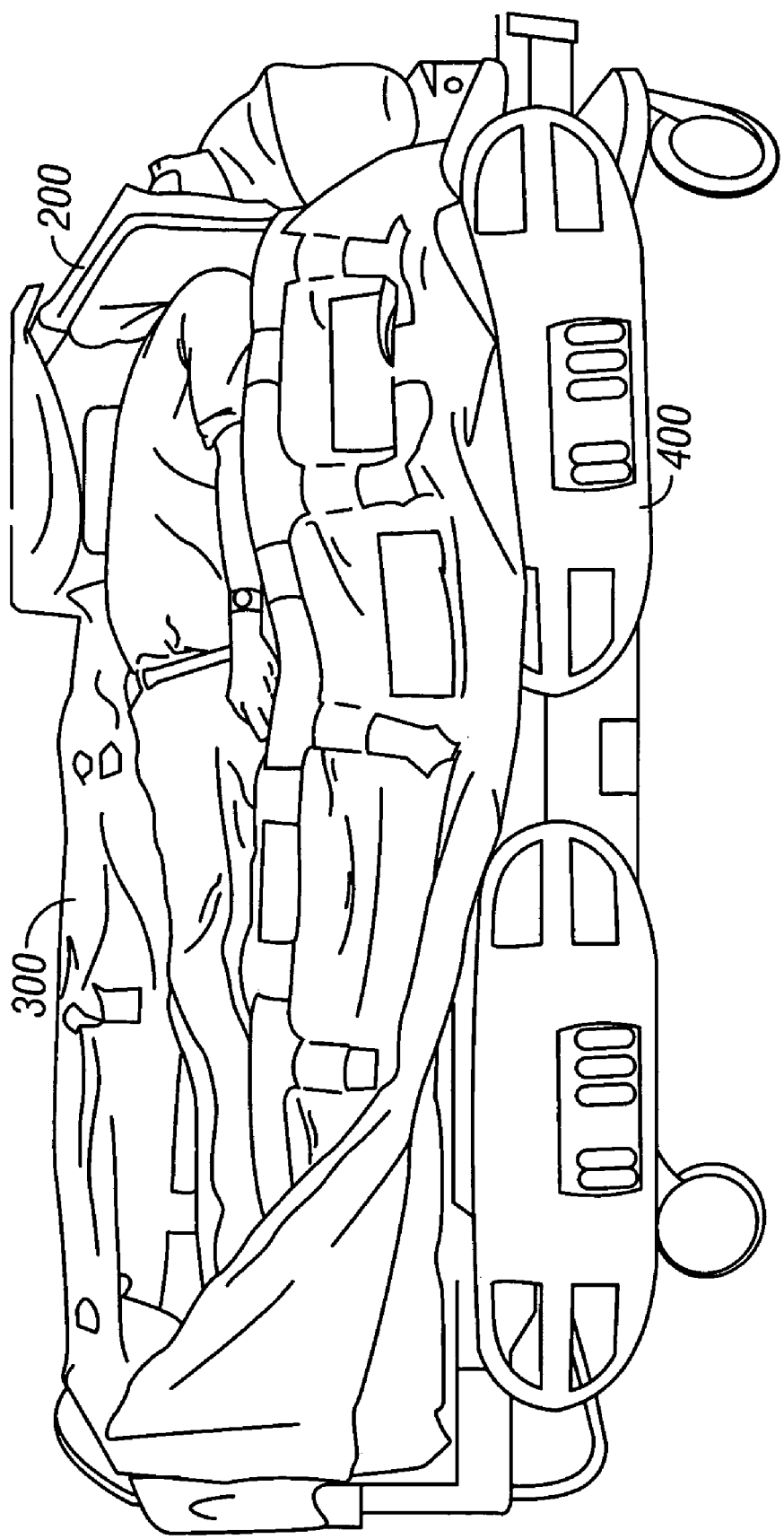
FIG. 11 is a side view of the patient support enclosure of FIG. 10 with one side folded down.
Figure 12:
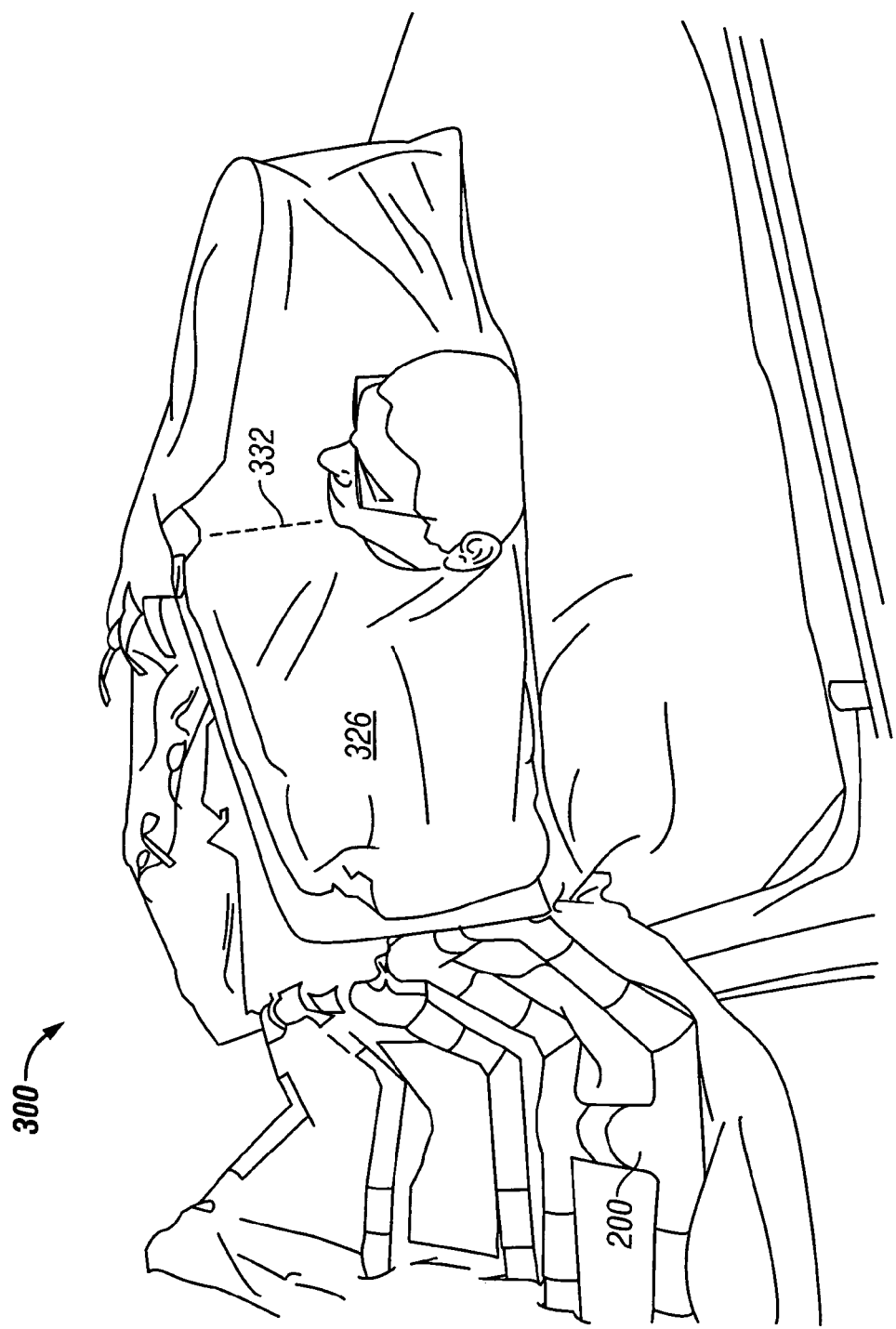
FIG. 12 is a head-end view of the patient support enclosure of FIG. 10 with one side folded down.

FIGS. 10 through 12 show an embodiment of a patient cooling enclosure comprising the air tent 300 of FIG. 9 with the tubular support framework 200 (FIG. 7) mounted on an articulating bed frame 400. FIG. 10 shows the air tent 300 in a closed position mounted on a frame in an articulated position. FIGS. 11 and 12 show the air tent 300 in an open position, with the left longitudinal half 250 of the still-inflated framework 200 folded away from the patient to provide access to the patient.

Figure 13A:
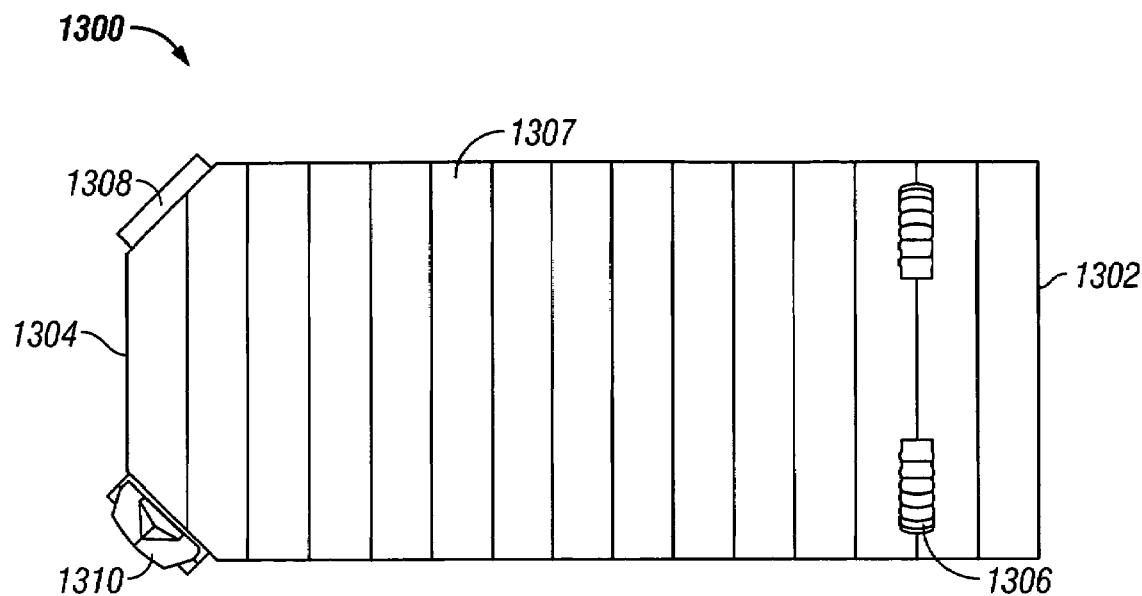
FIG. 13A is a top plan view of a mattress according to one embodiment of the present disclosure.
Figure 13B:
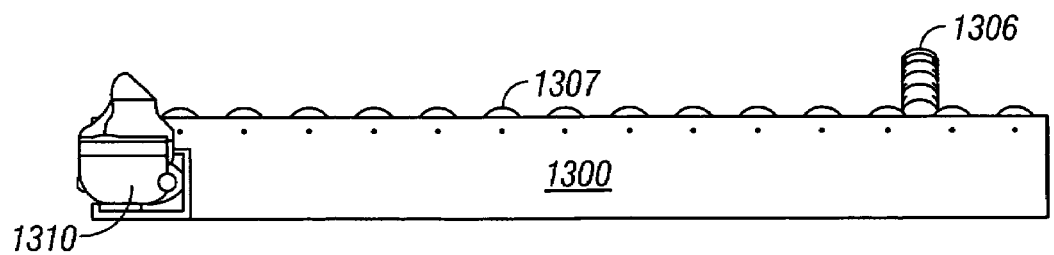
FIG. 13B is a side view of the mattress of FIG. 13A.

Referring now to FIGS. 13A and 13B, a top plan view and a side view, respectively, of a mattress 1300 according to one embodiment of the present disclosure is shown. The mattress 1300 includes a head end 1302 and a foot end 1304. Proximal the head end 1302 and mounted on opposing sides of the mattress 1300 are located a plurality of flexible vent hoses 1306 adapted to direct thermally controlled air onto a patient. It is preferable that the hoses 1306 are pointed towards a patient's neck, but other directions, such as the patient's trunk, extremities, or head are contemplated to be within the scope of this invention. As described above, the mattress includes a plurality of inflatable compartments or cells 1307 to which air is supplied.

Two circulation ports 1308 are provided at corners of the foot end 1304 of the mattress 1300. The circulation ports 1308 are adapted to universally connect to both a thermal control unit (not shown) and to a recirculation duct 1310. Orientation of the thermal control unit and recirculation duct 1310 is left to the discretion of the user, as more thoroughly described herein below. The circulation ports 1308 function to allow air to inflate the mattress and cool the patient, and to pull air out of the tent described herein above.

Figure 13C:
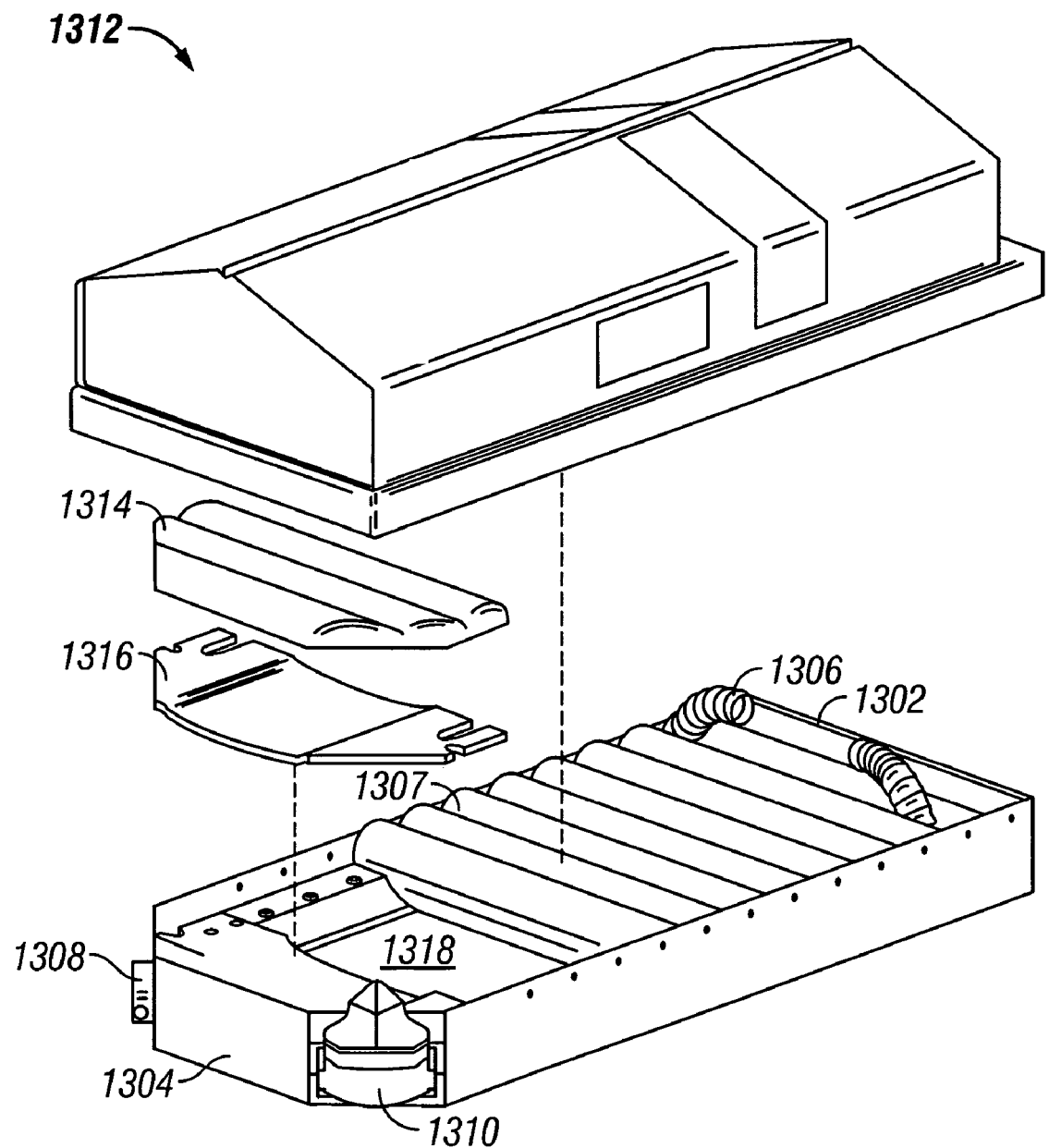
FIG. 13C is an exploded view of the mattress of FIG. 13A coupled to a tent according to one embodiment of the present disclosure.

Referring to FIG. 13C, an exploded view of the mattress 1300 coupled to an exemplary tent 1312 is shown. The mattress 1300 includes a separate inflatable lower section 1314 positioned over a foam base 1316, which itself is positioned over an air system cover 1318. The air system cover 1318 houses an air system as described below, such that the air flow of the mattress 1300 and tent 1312 combination is manifolded within the mattress 1300.

Figure 14A:
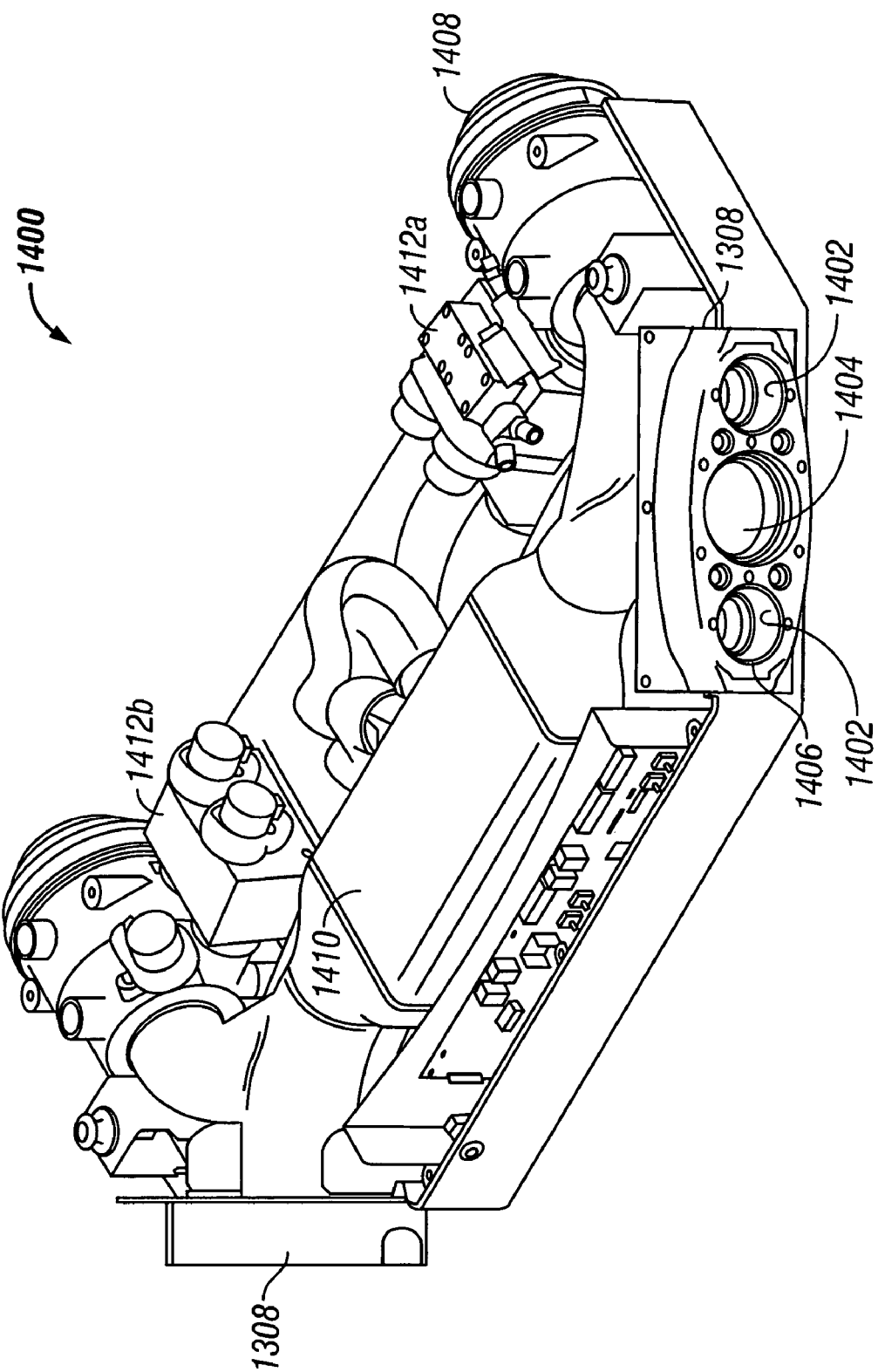
FIGS. 14A and 14B are respectively perspective views of an air flow system according to one embodiment of the present disclosure.
Figure 14B:
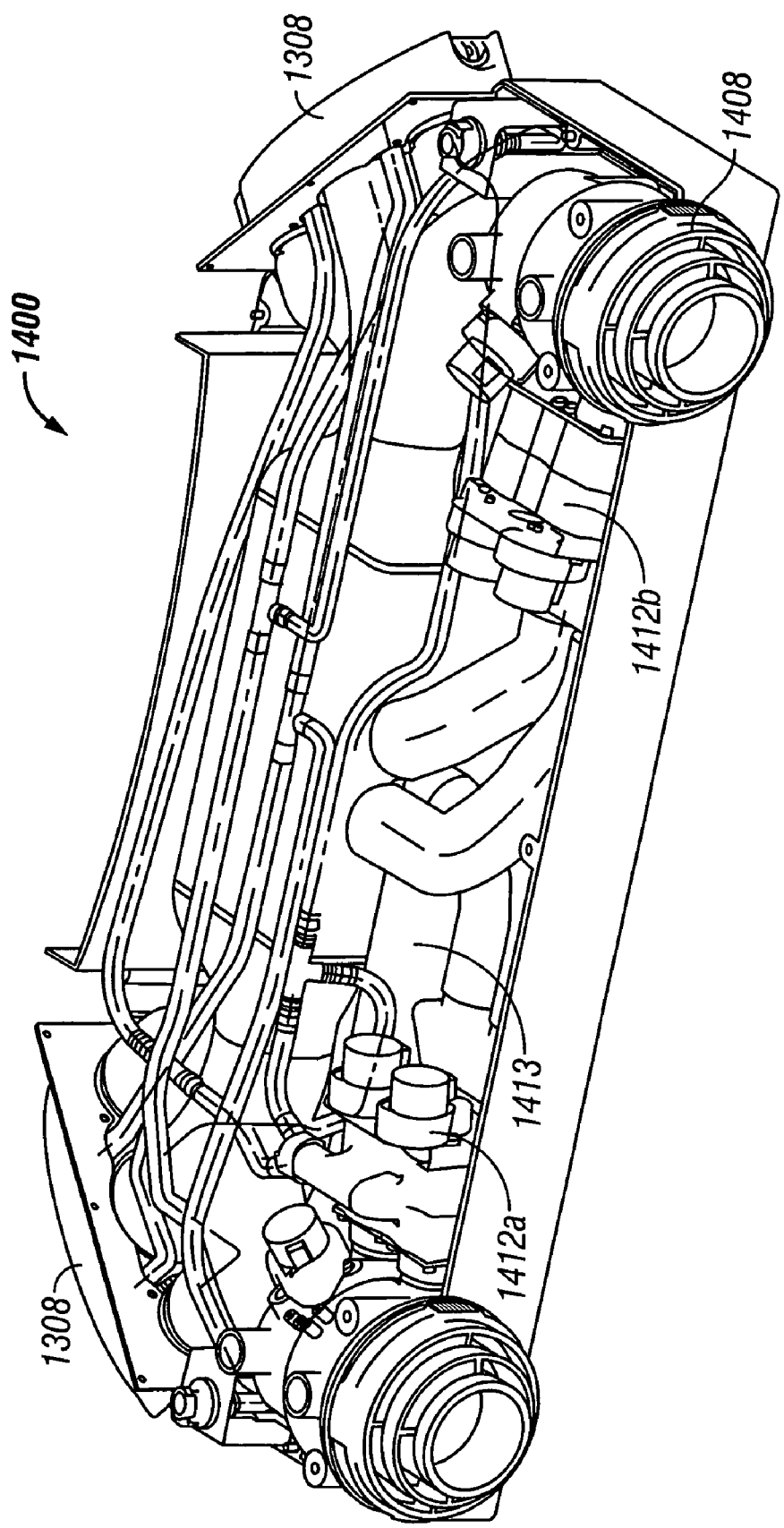

Referring to FIGS. 14A and 14B in combination, a perspective view of an air system 1400 adapted to be incorporated into the mattress 1300 (FIG. 13) is shown. Referring to FIGS. 13A-C in combination with FIGS. 14A and 14B, the circulation ports 1308 each have two outlet ducts 1402, a central duct 1404, and a plurality of high pressure ducts 1406. The air system 1400 further includes manifold connectors 1408, which direct flow to the mattress 1300 to the cells 1307, (FIG. 13) the vent hoses 1306 or to the inflatable support members of the tent 1312 itself as described herein above via central manifolds (not shown). The circulation port 1308 takes air from the thermal control unit (not shown) and splits the flow into the desired portion of the mattress or tent through the central duct 1404 and high pressure ducts 1406. This may happen via the air system inlet duct 1410, which connects to the central duct 1404, or via-valves 1412a, 1412b.

Valve 1412a operates between two positions: low pressure open and high pressure open. When the valve 1412a is set to low pressure open, it allows the flow of low pressure high flow air out of the central manifold (not shown) and into the central outlet duct (1413 of FIG. 14B) which is positioned beneath the inlet duct 1410. When the valve 1412a is set to high pressure open it allows the flow of high pressure low flow air into the central manifold. The outlet duct positioned beneath the inlet duct 1410 takes low pressure high flow air from valve 1412a and air from inside the tent 1312 (FIG. 3) and directs it back to the thermal control unit.

Valve 1412b is a combined valve that operates between two positions: fully open and fully closed. When the valve 1412b is set to fully open, it allows the flow of low pressure high flow air. When valve 1412b is set to fully closed high pressure low flow air flows through the air system 1400. FIG. 14b is another perspective view of the air system 1400 shown from a different angle than that of FIG. 14a and having flow lines 1414 connected to respective components described above.

Figure 15:
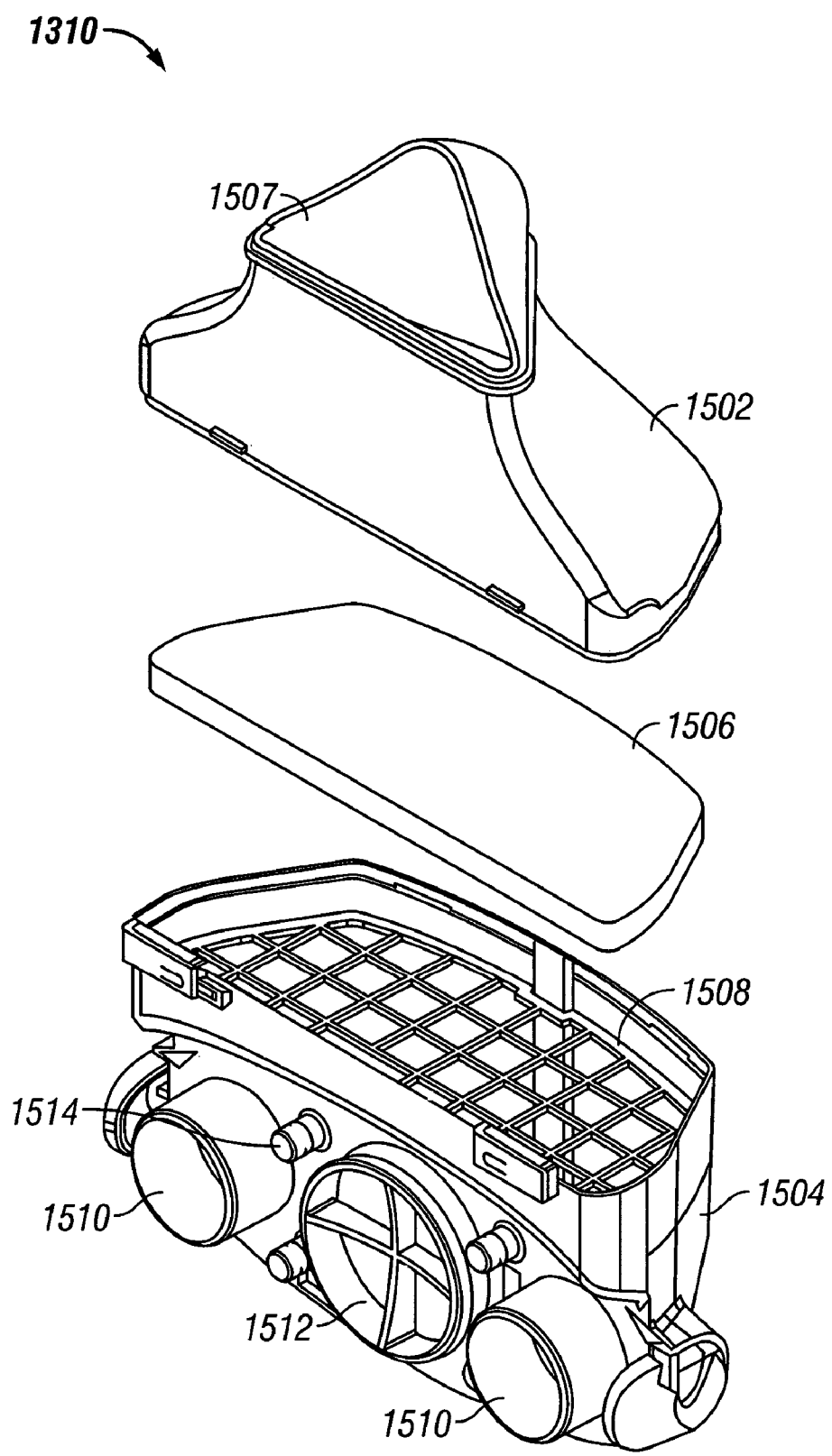
FIG. 15 is an exploded view of a recirculation duct according to one embodiment of the present disclosure.

Referring now to FIG. 15, an exploded view of the recirculation duct 1310 is shown. The recirculation duct 1310 includes an upper portion 1502, a lower portion 1504, and a recirculation filter 1506 positioned between the upper portion 1502 and the lower portion 1504. The upper portion 1502 has an opening 1507 adapted to allow airflow from the tent through the recirculation duct 1310. As the air flows through the recirculation duct 1310, particles in the air are removed via the recirculation filter 1506, which rests on a filter support tray 1508 positioned in the lower portion 1504 of the recirculation duct 1310. The filter support tray 1508 has a plurality of openings 1510 thereon to allow air to flow freely therethrough. The recirculation filter 1506 may be any suitable filter capable of effectively filtering airflow in a medical environment.

The lower portion 1504 includes outlet ports 1510 adapted to mate with the outlet ports 1402 of the air system 1400 (FIG. 14a), an inlet port 1512 adapted to mate with the inlet port 1404 of the air system 1400, and high pressure ports 1514 adapted to mate with the corresponding high pressure ports 1406 of the air system 1400. The recirculation duct 1310 is adapted to be connected to the air system 1400 at either end of the air system 1400.

Figure 16B:
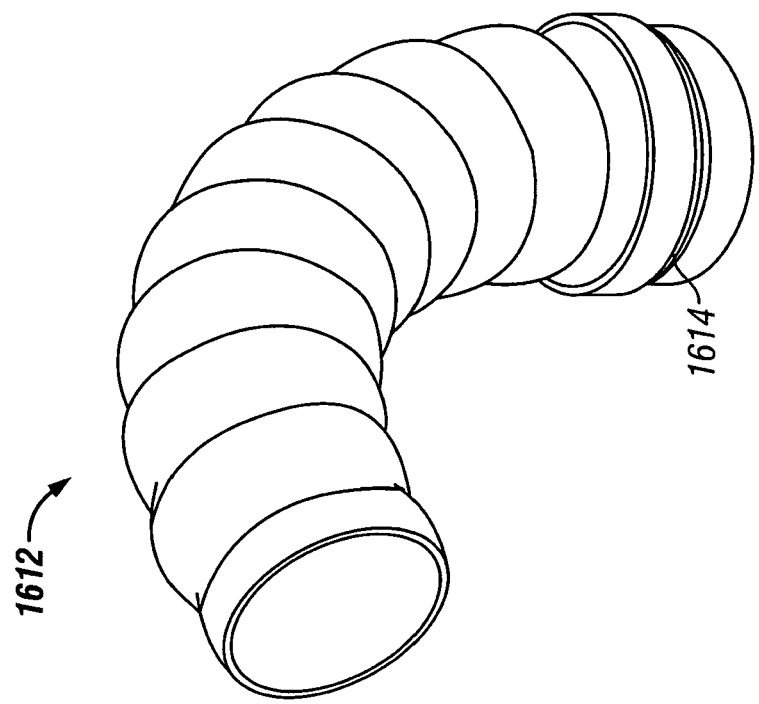
FIG. 16B is a perspective view of a vent hose assembly according to one embodiment of the present disclosure.
Figure 16A:
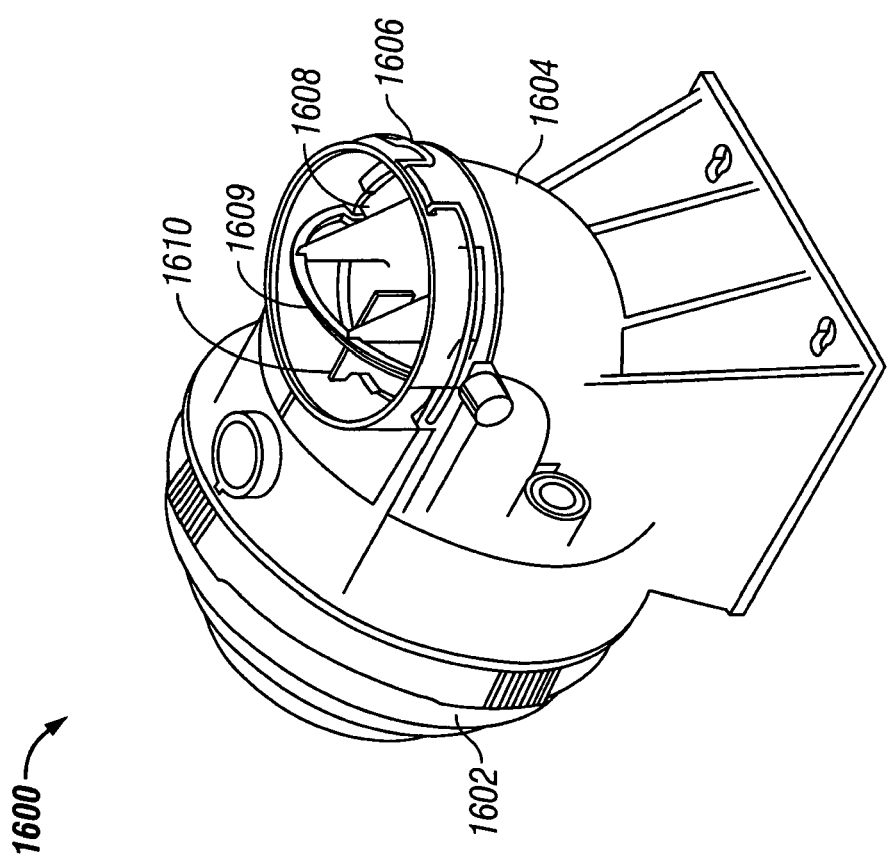
FIG. 16A is a perspective view of an elbow assembly incorporated into the mattress of FIG. 13A.

Referring now to FIG. 16A, a perspective view of an elbow assembly 1600 is shown, which is adapted to be coupled to a mattress frame as described herein. The elbow assembly 1600 includes a manifold connection portion 1602, and a vent portion 1604 connected to the manifold connection portion 1602. The vent portion 1604 is adapted to re-direct airflow from the central manifold (not shown) through the manifold connection portion 1602. The vent portion 1604 includes a spring 1606, which in turn is connected to a butterfly flap 1608 positioned in the vent portion 1604. The butterfly flap 1608 is biased in a closed position, but is adapted to open with relative ease. A hoop bar 1609 is connected to an upper surface of the butterfly flap 1608 to facilitate opening and closing of the butterfly flap 1608. A stop rib 1610 is also provided on the butterfly flap 1608 to prevent the butterfly flap 1608 from moving beyond a predetermined position to enable closing of the elbow assembly 1600. The stop rib 1610 further prevents attachment of any component to the elbow assembly 1600 when the butterfly flap 1608 is in a closed position.

Referring to FIG. 16B, a perspective view of a vent hose 1612 is shown. The vent hose 1612 is adapted to be coupled to the elbow assembly 1600, and is flexible, such that a user may position the vent hose 1612, for example, at a patient's neck, trunk, other body part, or away from the patient, should circumstances require. A groove 1614 is machined at the base of the vent hose 1612 to facilitate coupling of the vent hose 1612 to the elbow assembly 1600.

Figure 17B:
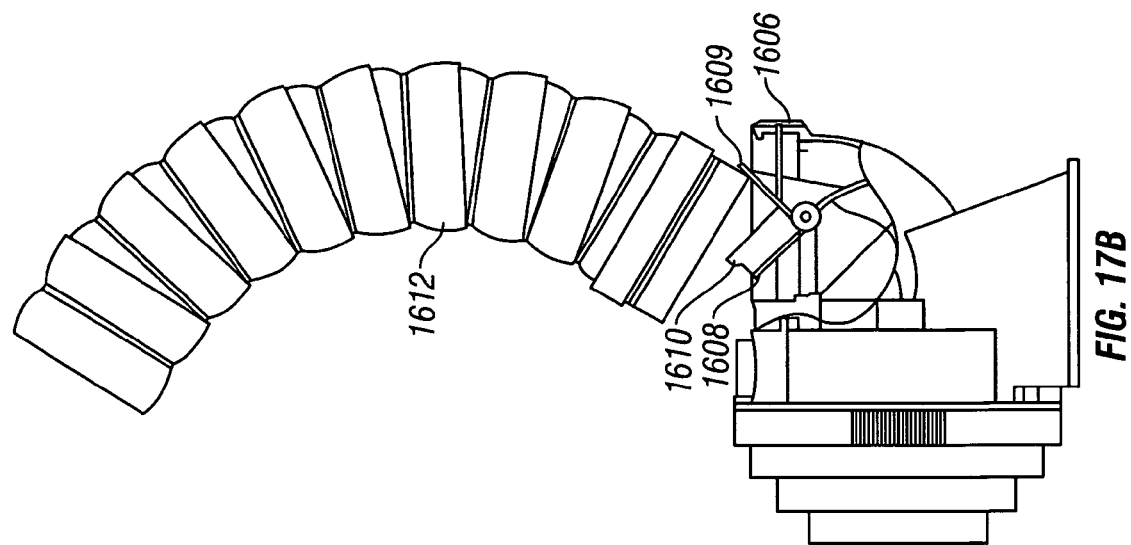
FIGS. 17A-D are side views of the vent hose and elbow of FIGS. 16A-B in various connection stages.
Figure 17A:
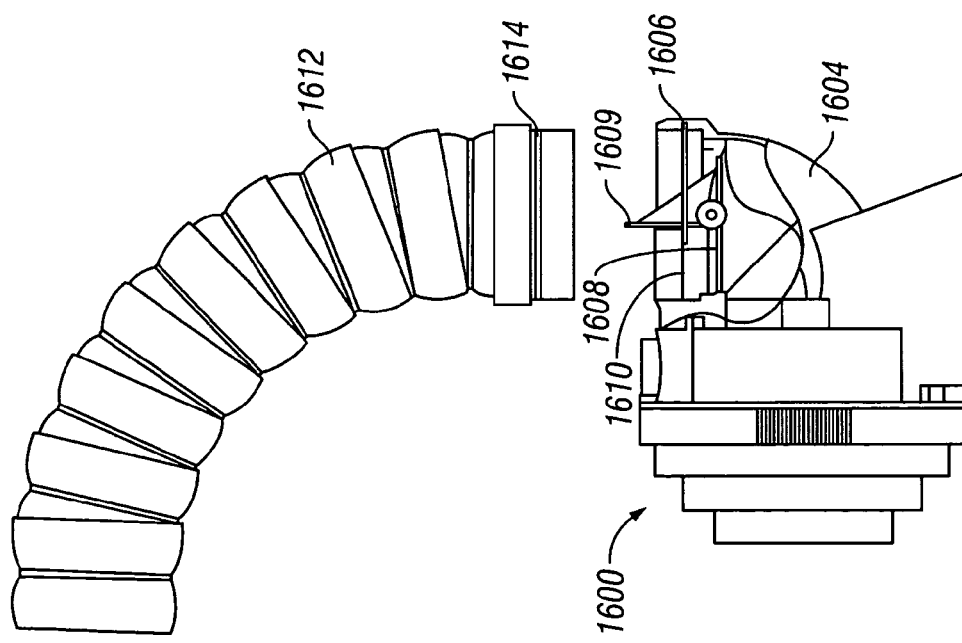
Figure 17D:
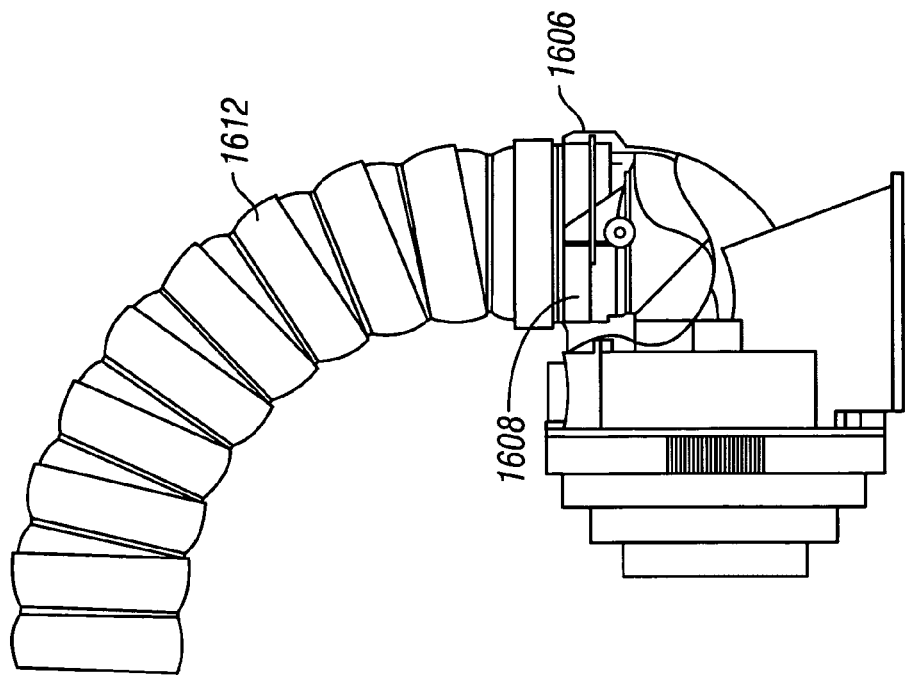
Figure 17C:
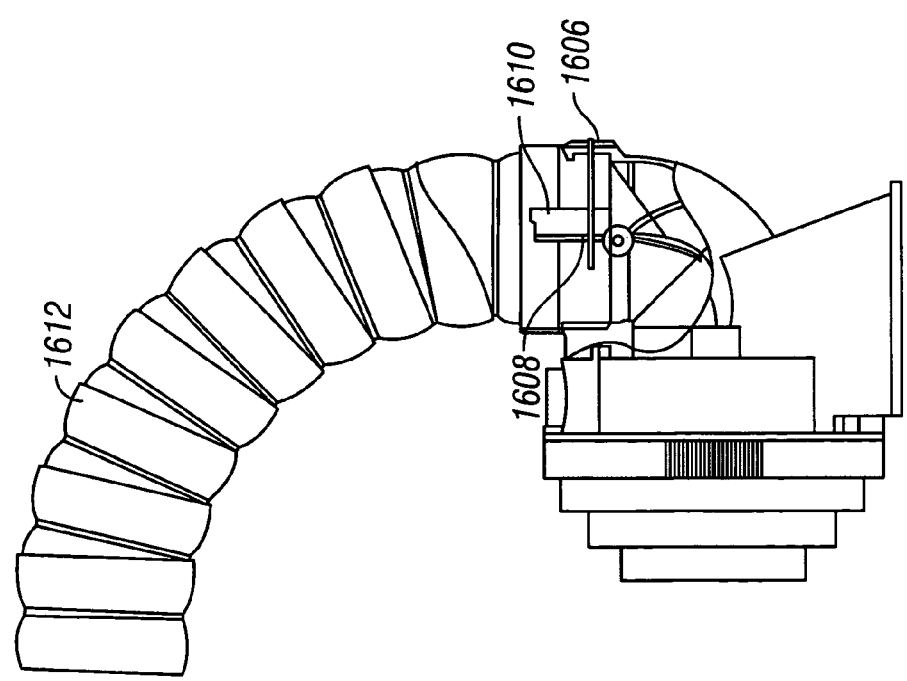

Referring now to FIGS. 17A-D, side views of the vent hose 1612 and elbow assembly 1600 of FIGS. 16A-B is shown in various connection stages. Referring specifically to FIG. 17A, the elbow assembly 1600 is shown in a closed position prior to attachment to the vent hose 1612. In FIG. 17B, the vent hose 1612 is used to apply pressure onto the hoop bar 1609 to bias the butterfly flap 1608 in an opening configuration. FIG. 17C is a partial cutaway side view of the elbow assembly/vent hose, showing the butterfly flap 1608 in an open position after connection of the elbow assembly/vent hose. FIG. 17D is a side view of the elbow assembly/vent hose after connection. Removal is easily achieved by pulling the vent hose 1612 out of the bore of the elbow assembly 1600. When the vent hose 1612 is removed from the elbow assembly 1600, the butterfly flap 1608 closes due to the force of the spring 1606. The spring is also used to retain the vent hose 1612, yet still allow rotation of the vent hose 1612 within the bore of the elbow assembly 1600. As a safety feature, if an attempt is made to insert the vent hose 1612 without opening the butterfly flap 1608, full engagement is prevented by the stop rib 1610.

Figure 18:
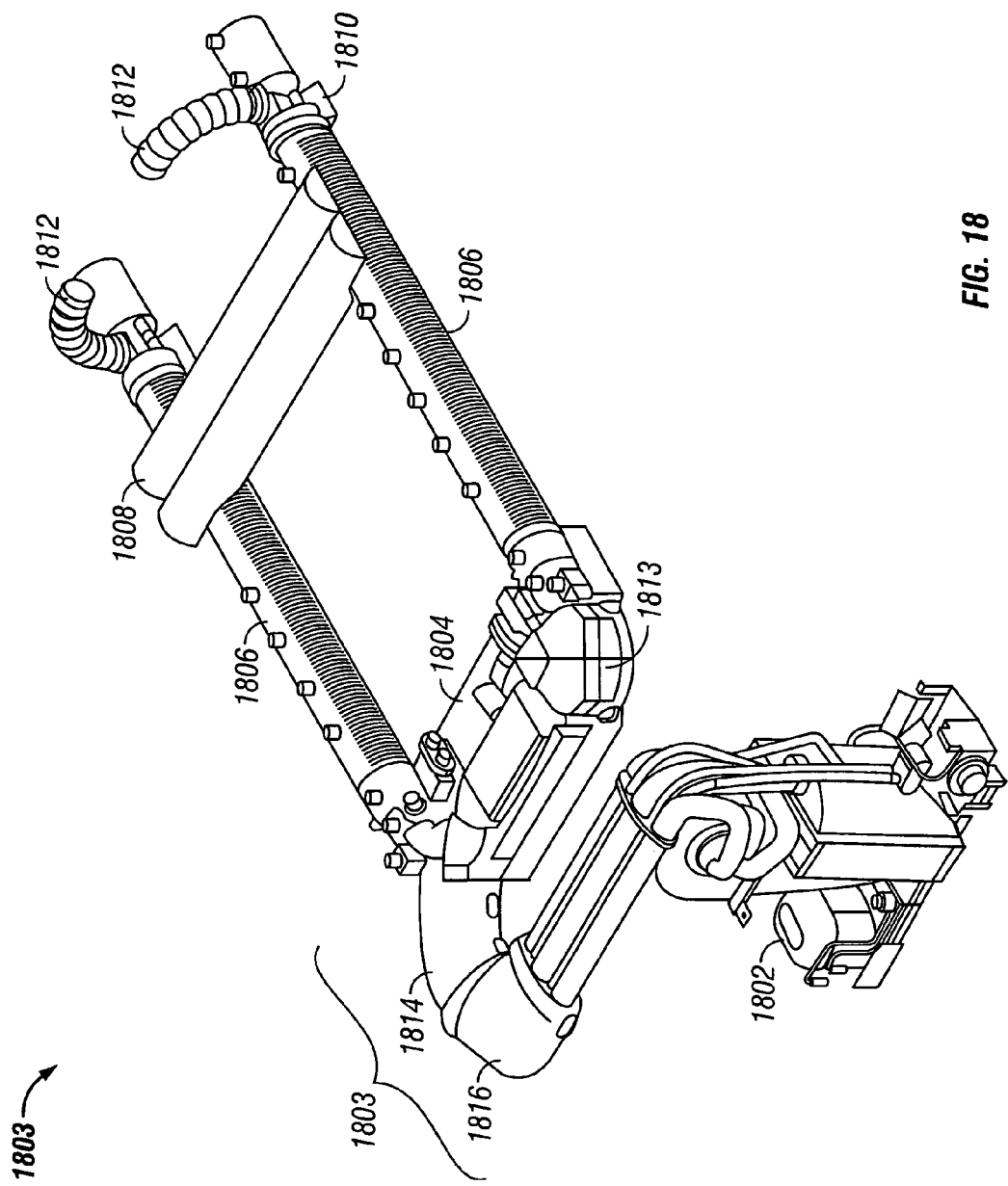
FIG. 18 is a perspective view of a partially assembled mattress of FIG. 13A connected to a thermal control unit.

Referring now to FIG. 18, a perspective view of one embodiment of a partially assembled mattress and flow system 1800 is shown. The flow system 1800 includes a thermal control unit (TCU) 1802, connecting the TCU 1802 to the connection interface 1803 to air system 1804, which connects to two central manifolds 1806. The central manifolds 1806, which run along the length of the mattress, in turn connect to the air cells 1808 and to the elbow assembly 1810. The elbow assembly, in turn, connects to the vent hose 1812, which directs air into the tent (not shown). The recirculation duct 1813 is shown at one corner of the mattress proximal the foot portion of the flow system 1800. On the other corner connected to the air system 1814 via the connection interface 1803, which may comprise 45 degree and 90 degree connectors 1814, 1816 respectively, is the TCU 1802.

The TCU 1802 functions both to provide cool or warm air to the air cells 1808 via central manifolds 1806 and to the tent (not shown) via the vent hoses 1812. The TCU 1802 also functions to remove air from the tent via the recirculation duct 1813. Finally, the TCU 1802 also provides air to the tent (not shown) to maintain the tent structure during operation. It is important to note that the 45 degree and 90 degree connectors 1814, 1816 may be connected to either end of the air system 1804, thereby providing many different orientation capabilities of the TCU 1802 in relation to the air system 1804, described in more detail below. It is further to be understood that only one connector may be required depending on space limitations, and the modular nature of the connectors and interchangeability provide for a large number of orientations.

Figure 19:
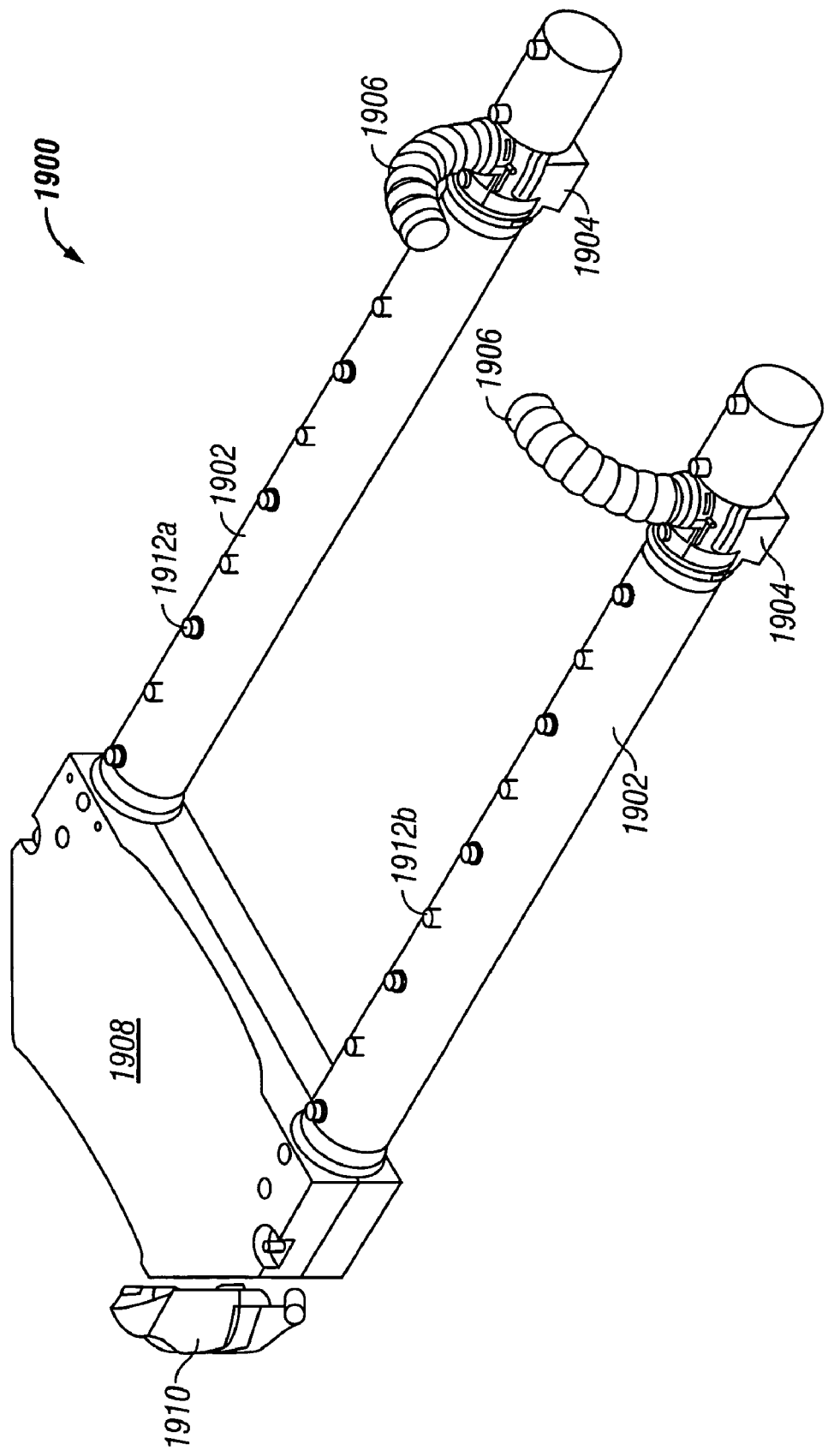
FIG. 19 is another perspective view of a partially assembled mattress of FIG. 13A having a cover over the air system.

Referring now to FIG. 19, another perspective view of a partially assembled mattress 1900 is shown. The partially assembled mattress 1900 includes the central manifolds 1902 that run the length of the fully assembled mattress (FIG. 20), which connect at one end to a respective elbow assembly 1904 and vent hose 1906, and at the other end to the air system (not shown). The air system is housed by a protective cover 1908, which protects the components of the air system during use. Connected at one corner of the housing is a recirculation duct 1910, which functions in the same manner as described herein above.

The top portion of the central manifolds 1902 include outlet ports 1912a, 1912b, which are adapted to connect to alternating air cells (FIG. 18). Alternate air cells may be connected to alternate outlet ports 1912 on the opposite central manifold 1902 to provide for separate inflation/deflation as described herein above. The outlet ports 1912 further provide a means for the air cells to deflate quickly in emergency situations, should circumstances require.

Figure 20:
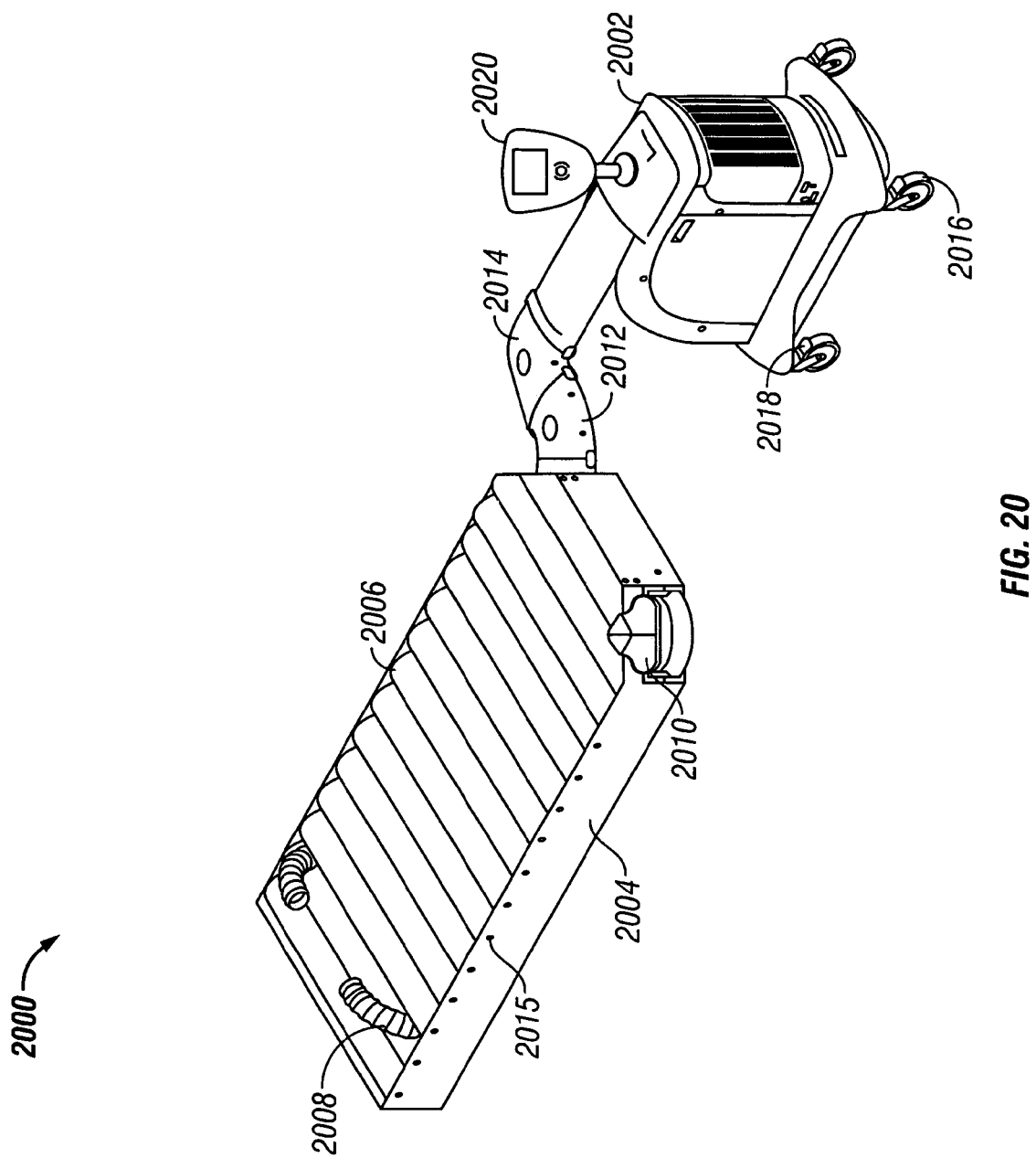
FIG. 20 is a perspective view of the assembled mattress of FIG. 13A coupled to the thermal control unit of FIG. 19.

FIG. 20 is a perspective view of an assembled mattress 2000 coupled to a thermal control unit 2002. The mattress 2000 includes a mattress frame 2004, which in turn houses the air system (not shown) and air cells 2006, which extend transversely across the mattress 2000. The air cells 2006 have openings (not specifically shown) which allow the vent hoses 2008 to extend therethrough and be positioned in any configuration as desired by the user. A recirculation duct 2010 is shown attached at one corner of the mattress 2000. At another corner, the TCU 2002 is connected via a 45 degree connector 2012 and a 90 degree connector 2014, although the number of connectors and the degree orientation of the connectors is not intended to be limited by this drawing. A plurality of snap buttons 2015 are provided along the perimeter of the mattress frame 2004 to allow connection to a tent, such as the one shown in FIG. 12 for example.

The TCU 2002 may include wheels 2016, such as caster wheels or the like, to enable ease of moving the TCU 2002 around the environment. Safety locks 2018 may be provided on the wheels 2016 to lock the TCU 2002 in place relative to the mattress 2000. An interactive display 2020 is provided on the TCU 2002 to allow a user to control and monitor the settings of the therapy provided by the mattress/tent combination. The display 2020 also has alarm indicators for adverse events, should they occur. The display 2020, which is preferably touch-screen, also allows for quick inflation/deflation of the tent and mattress 2000 should circumstances require.

Referring now to FIGS. 21A-I, top plan views of the mattress/thermal control unit assembly 2100 are shown in various orientations to illustrate exemplary orientation of the TCU 2102 relative the mattress 2104. It is to be understood and appreciated that an air tent, such as that of FIG. 12, is connected to the mattress to provide the environment for thermal control of the patient. It is to be further understood that these orientations are exemplary, and are not limiting, as the possible variations of connection exceed what is shown in these Figures for example purposes.

Figure 21A:
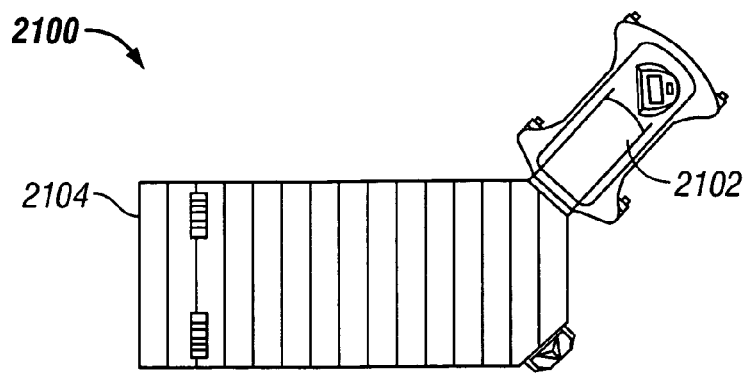
FIGS. 21A-I are top plan views of the mattress/thermal control unit in various orientations.
Figure 21B:
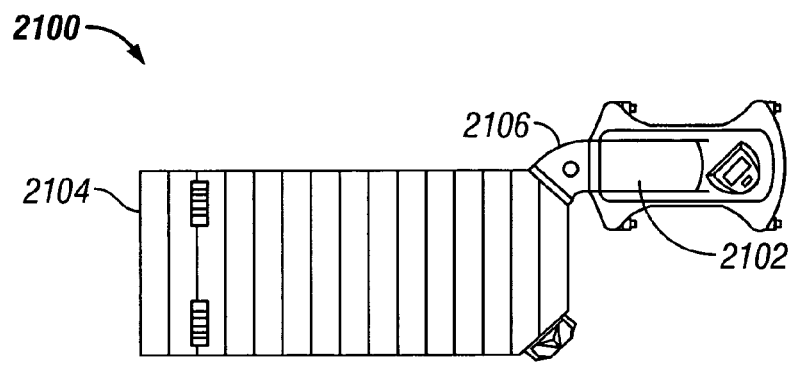
Figure 21C:
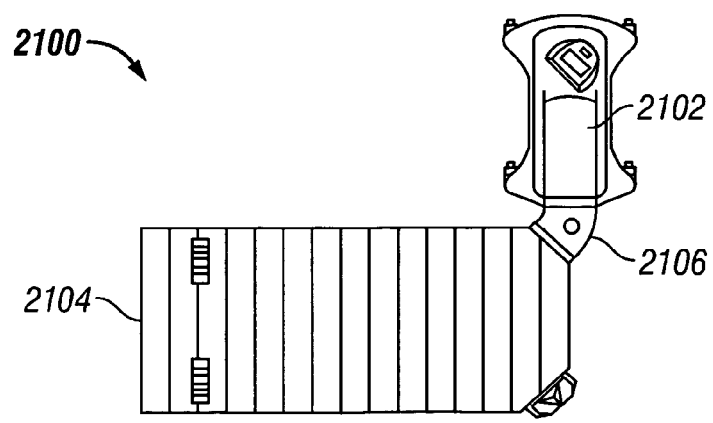
Figure 21D:
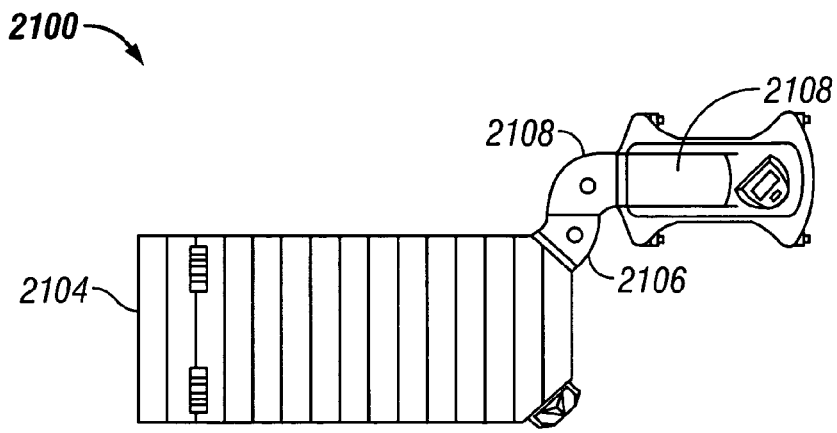
Figure 21E:
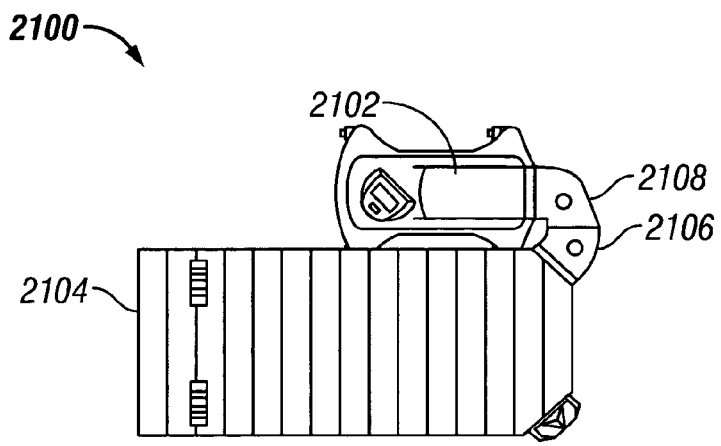
Figure 21F:
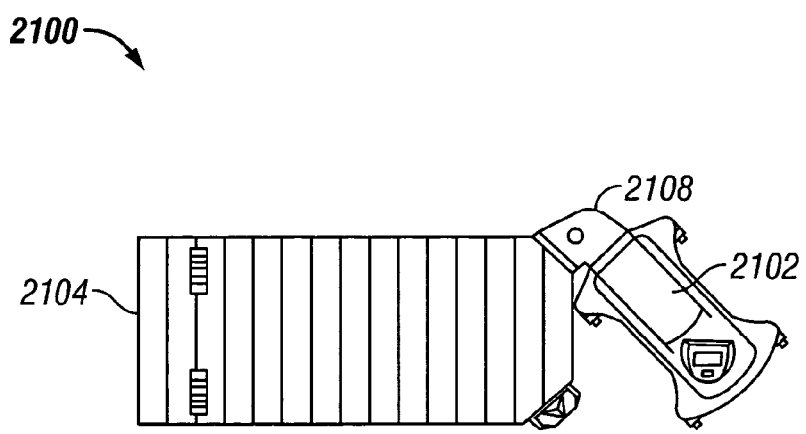
Figure 21G:
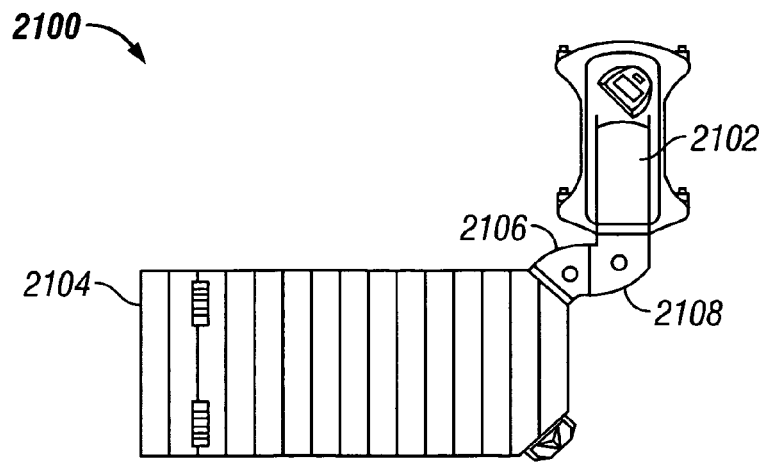
Figure 21H:
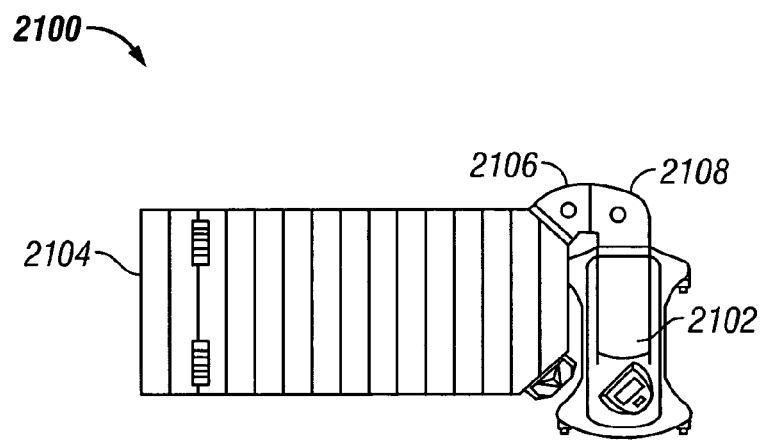
Figure 21I:
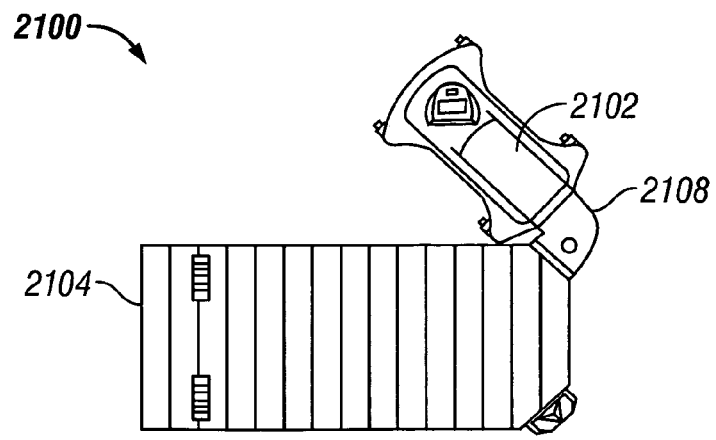

FIG. 21A shows the TCU 2102 directly connected to the mattress 2104 without any connectors. FIG. 21B illustrates the TCU 2102 connected by a 45 degree connector 2106 to the mattress 2104. FIG. 21C likewise illustrates the TCU 2102 in a 45 degree connection to the mattress 2104 via a 45 degree connector 2106. FIG. 21D illustrates the use of a 45 degree connector 2106 and a 90 degree connector 2108 for locating the TCU 2102 in a different configuration. FIGS. 21E-I illustrate various exemplary configurations for the TCU 2102 relative the mattress 2104. It is to be appreciated that space in medical rooms is limited, and as a result, the modular connections provided by the invention herein will accommodate such limitations.

Figure 22:
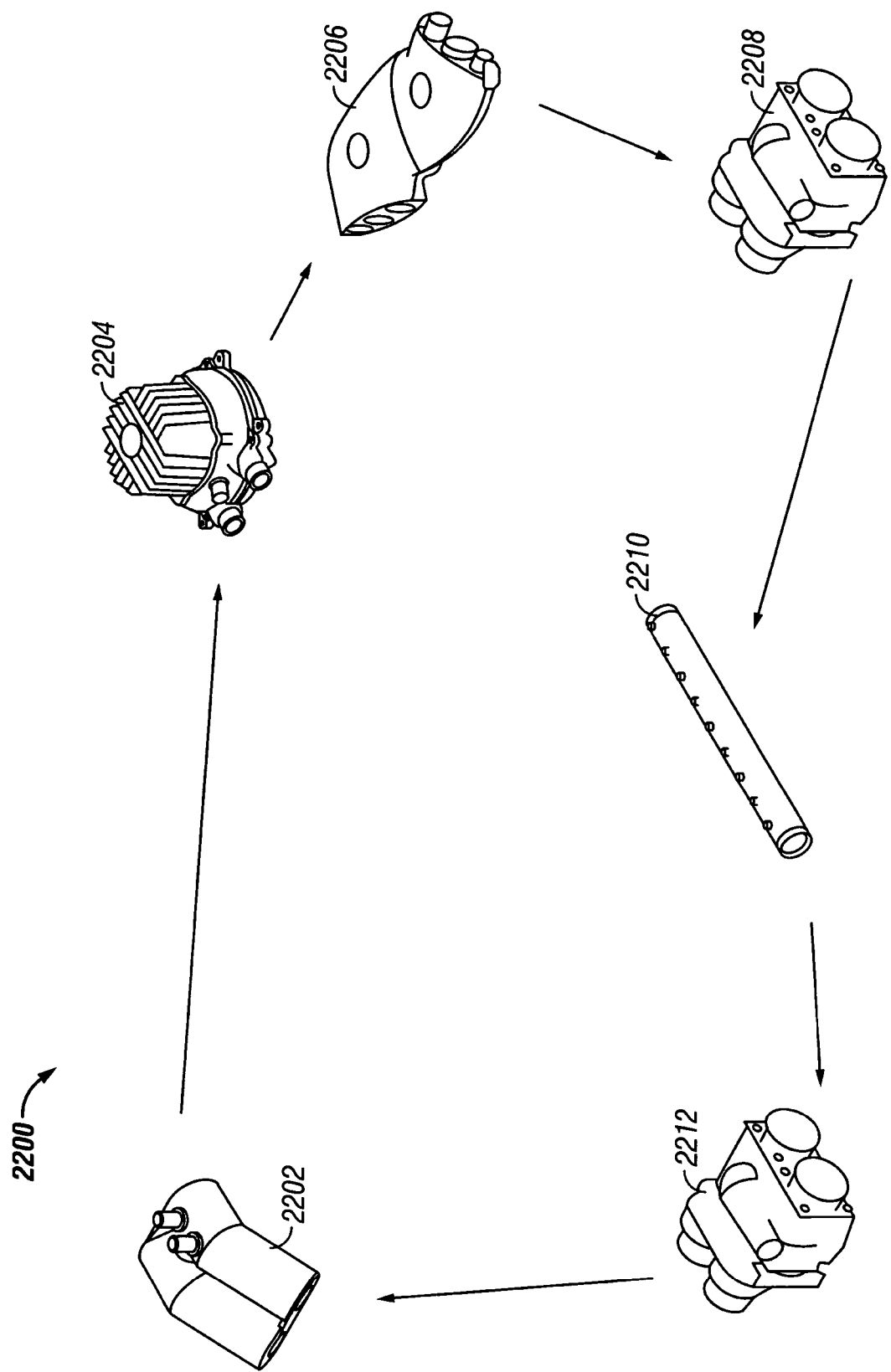
FIG. 22 is a diagrammatic illustration of high pressure air flow according to one embodiment of the present disclosure.

Referring now to FIG. 22 is a diagrammatic illustration of high pressure air flow cycle 2200 is shown according to one embodiment of the present disclosure. First, air is drawn into the TCU (not shown) via silencer 2202, which allows for a reduction in the noise of the TCU during operation. Next, air is compressed with a blower 2204. The air flow is then transferred between the TCU and the mattress either directly or via one or more connectors 2206. Air flow then enters the air system, where it is diverted into valve 2206 which diverts the flow to mattress air cells via one channel of the central manifold 2208. Valve 2210 blocks air flow to maintain pressure in the mattress air cells, but when the flow cycle changes, opens to allow air to be exhausted either back to the TCU or to the environment. The central manifold 2208 as described herein is multi-channeled to allow the provide for the different flow requirements.

Figure 23:
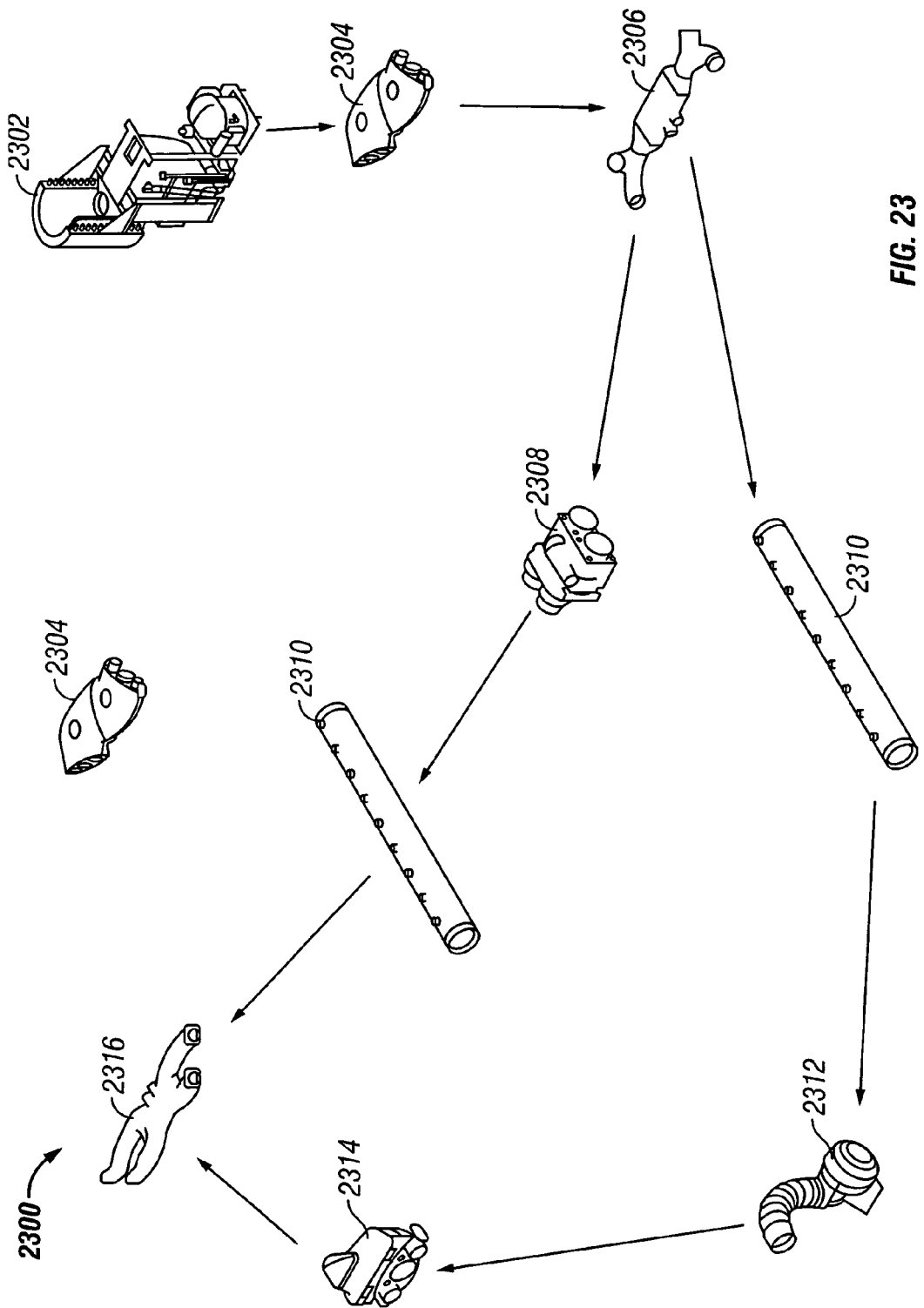
FIG. 23 is a diagrammatic illustration of low pressure air flow according to one embodiment of the present disclosure.

Referring now to FIG. 23, a diagrammatic illustration of low pressure air flow cycle 2300 with recirculation is shown according to one embodiment of the present disclosure. Air flow is introduced into the TCU 2302, where it is cooled or heated and dehumidified. It is next transferred directly between the TCU 2302 and mattress, where connectors 2304 may be used. Air flow is split into mattress flow and the vent hose flow via the inlet duct 2306.

For the vent hose flow, air flow is directed to the vent hoses using the central channel of the central manifold 2310. Air flow is then directed at the patient to thermally control the patient via the vent hose/elbow assembly 2312. Air flow travels within the tent environment to the foot end of the mattress, where it is pulled into the recirculation duct 2314.

For the mattress flow, depending on the cycle of cell inflation valve 2308 diverts the air flow to the appropriate outer channel of the central manifold 2310 and to the mattress air cell. Air flow then returns through the opposite outer channel of the central manifold 2310 where it merges with recirculated air from the recirculation duct 2314 in the outlet duct 2316. Air flow is then transferred between the mattress and TCU 2302 directly or via connectors 2304. The air is then thermally controlled in the TCU 2302, where the cycle may be repeated.

Figure 24:
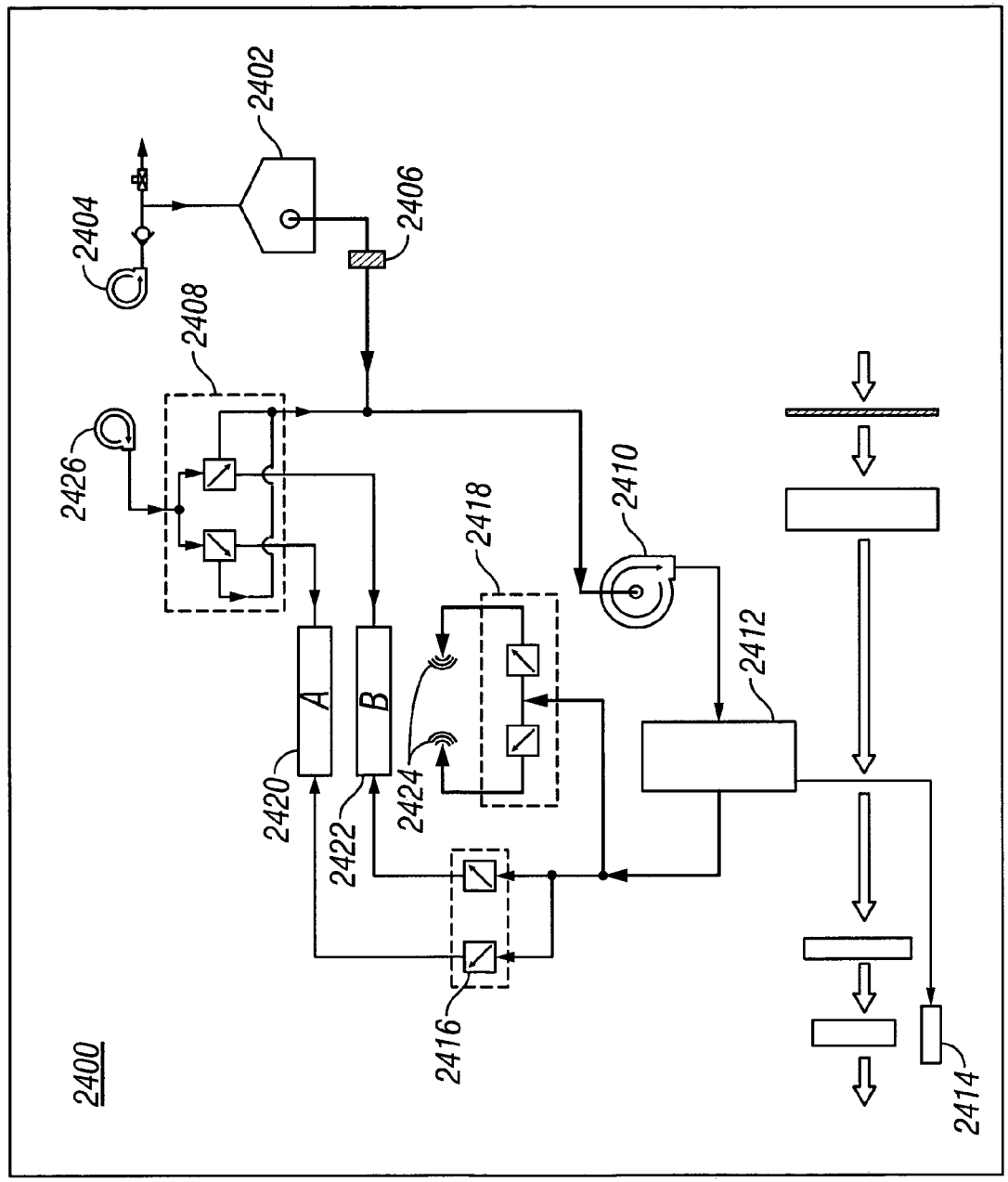
FIG. 24 is a schematic diagram of a patient cooling system according to one embodiment of the invention.

FIG. 24 is a schematic diagram of a patient cooling system 2400 according to the invention. Air flow is pumped into the air tent 2402 via tent pump 2404, where it is next recirculated after passing through a recirculation filter 2406. It is important to note that the recirculation filter 2406 may be integrally formed with the tent 2402 such that when a new tent 2402 is used for a new patient, the step of separately replacing the filter 2406 is eliminated. Valves 2408 control whether air is to be recirculated or exhausted. For recirculation, air next moves through a primary blower 2410, and is then thermally treated to make it cooler or warmer through an evaporator coil 2412. The evaporator coil 2412 has a removable condensation tray 2414 which may include an alarm system to alert the user when the tray 2414 is full. Air then is directed through valves 2416, 2418, which divert flow through mattress cells 2420, 2422 depending on the cycle, or back into the tent via the vent hose 2424, respectively. A high pressure pump 2426 is provided to provide high pressure air into the system 2400.

FIGS. 25A-25D illustrate various embodiments of a neck member of the present disclosure. The various embodiments of the neck member provide an improved method to provide thermal control to a patient. Providing thermal control to the patient can include lowering the temperature of the patient to a temperature below normal body temperature. Providing thermal control to the patient can also include warming the temperature of the patient to a temperature above normal body temperature. And, providing thermal control to the patient can include warming or cooling the temperature of the patient to normal body temperature, as for example, where the human body is above or below normal body temperature prior to providing thermal control to the patient.

Features of the neck member provide a controlled and efficient method to position the neck member for use on a patient and to direct thermally treated air, such as warm or cool air, to the patient's neck area. For example, features, such as the pivot points, work in conjunction with other components of the present disclosure to provide the neck member with the capability to move in various directions. In some embodiments, the neck member can pivot away from a patient's head while positioning the patient on the patient support. Once the patient is properly positioned, the neck member can pivot toward the patient's neck area to position the neck member for use on the patient, as will be described herein. Other features include openings defined by surfaces of the neck member, which direct and maintain thermally treated air (e.g., cooled air) on the patient's neck area; a region of the human body in which heat transfer (e.g., heat loss) is rapid. For example, in various embodiments, the neck member can include a number of portions These and other features of the neck member are described in FIGS. 25A to 26B.

Figure 25A:
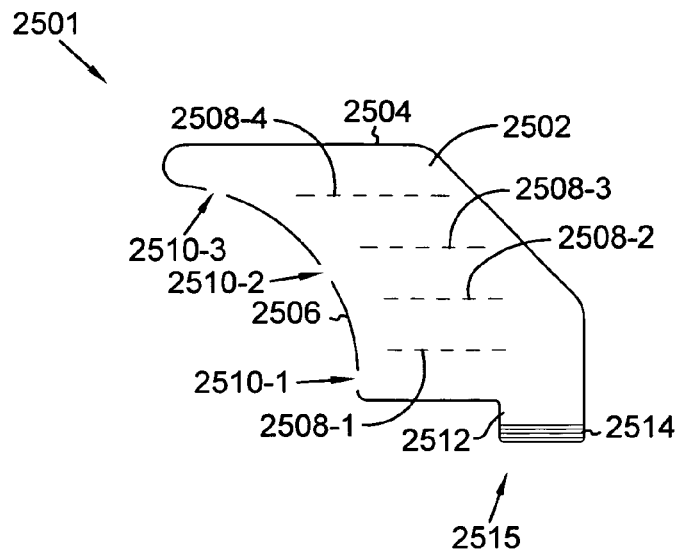
FIG. 25A provides a front view of a neck member according to one embodiment of the present disclosure.

Referring to FIG. 25A, a front view of neck member 2501 is illustrated. As shown in FIG. 25A, neck member 2501 includes a first member 2502. In various embodiments, the first member 2502 is inflatable and can include a variety of shapes and sizes. In the embodiment shown in FIG. 25A, the first inflatable member 2502 includes an irregular shape having number of planar surfaces and curved or arcuate surfaces. As will be discussed herein, one or more surfaces of the first inflatable member can define an opening.

The interior of the first inflatable member 2502 defines a chamber (not shown) that can be expanded when the first inflatable member is inflated. In various embodiments, the first inflatable member can include at least one baffle 2508 to support a shape of the first inflatable member when the first inflatable member is inflated. As shown in the embodiment illustrated in FIG. 25A, the first inflatable member has four baffles 2508-1 to 2508-4. In some embodiments, the baffles can also serve to direct air through openings in the first inflatable member, as will be discussed herein.

In various embodiments, the first inflatable member can include a surface defining at least one opening. In various embodiments, surfaces of the first inflatable member can include various shapes and sizes. For example, in the embodiment illustrated in FIG. 25A, surface 2506 has an arcuate shape and defines three openings 2510-1 to 2510-3. As will be discussed in more detail herein, the openings 2510 are in fluid communication with a source of thermally treated air (e.g., thermal control unit (TCU) 1802 in FIG. 18 or thermal control unit 2002 in FIG. 20) and function to direct air (e.g., warmed air, cooled air, and/or pressurized air) from the interior of first inflatable member 2502 and out the openings 2510. In various embodiments, the at least one opening 2510 can be positioned proximal to the neck area of the patient such that the flow of thermally treated air passing through the at least one opening 2510 is directed to skin on the neck area of the patient. In some embodiments, the flow of thermally treated air is cooled air to cool the patient to a temperature below normal body temperature.

The first inflatable member 2502 includes at least one air inlet 2512 to provide the thermally treated air to the first inflatable member 2502. In various embodiments, the air inlet 2512 can include an elongate member 2514 defining a lumen (not shown) coupleable to a source of thermally treated air (not shown). The elongate member 2514 can be configured in a number of ways. For example, in some embodiments, the elongate member 2514 can be a rigid, semi-rigid, or elastic hose having fasteners such as clips, threads, elasticated bands, among others, that can be used to couple the elongate member 2514 to other components of the present disclosure including a source of air. For example, in some embodiments, the air inlet can be a semi-rigid flexible hose that can fit over vent portion 1604 of elbow assembly 1600 illustrated in FIG. 16A and secured thereto using clamps and/or one or more elastic bands. In this embodiment, cool or warm air from an air source such as TCU, as discussed herein, can be introduced into the first inflatable member via the elongate member 2514 of the air inlet 2512.

Various portions of the air inlet 2512 can also function as a pivot point 2515 of the first inflatable member 2502 when the air inlet 2512 is coupled to the source of air. The pivot point allows the first inflatable member to pivot in a number of directions. For example, the pivot point 2515 of the first inflatable member 2502 allows an operator of the first inflatable member to pivot or move the first inflatable member out of the way of a patient's head when the patient is being positioned on a patient support surface, as discussed herein.

Figure 25B:
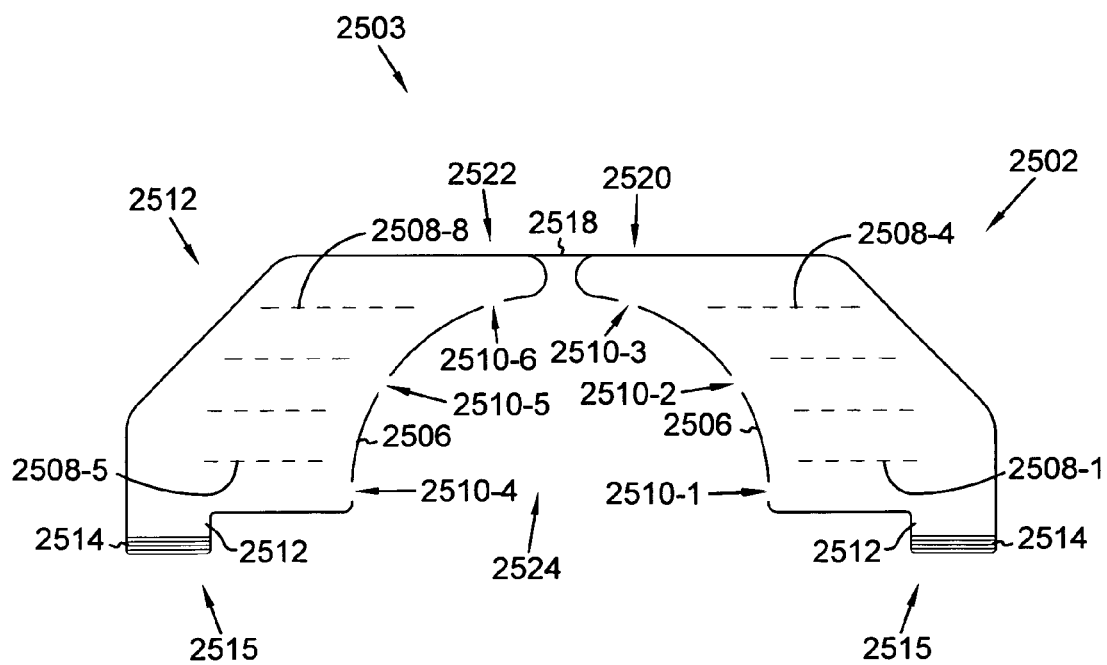
FIG. 25B illustrates another embodiment of a neck member of the present disclosure.
Figure 25C:
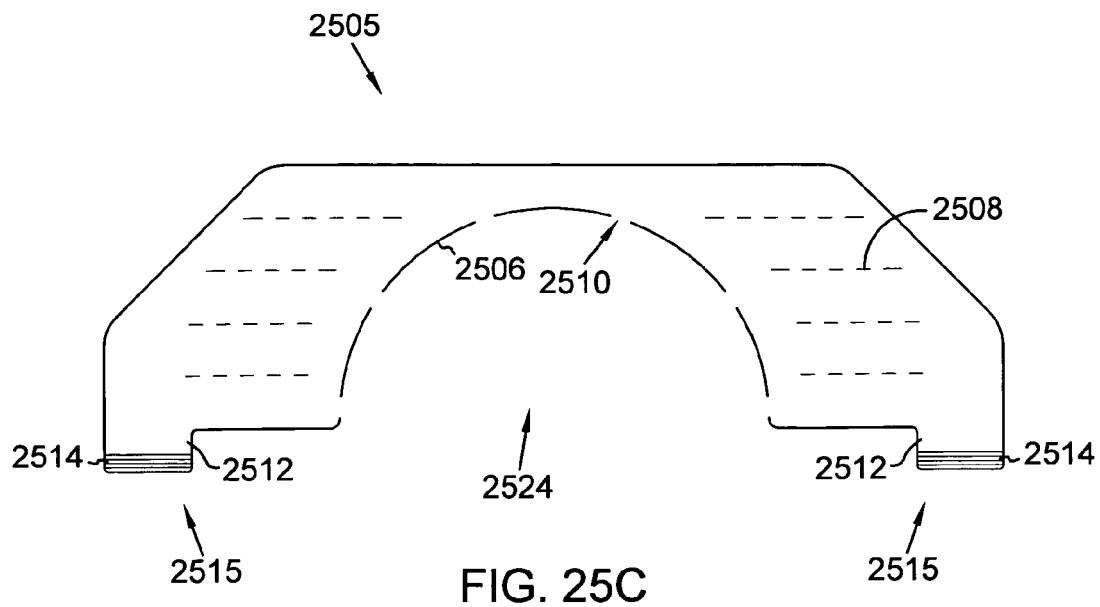
FIG. 25C illustrates another embodiment of a neck member of the present disclosure.

FIG. 25B illustrates another embodiment of a neck member 2503 to provide thermal control to a patient. As shown in FIG. 25B, neck member 2503 includes the first and a second member. In the embodiment illustrated in FIG. 25B, the first and second members 2502 and 2512 are inflatable. In various embodiments, the second inflatable member 2512 includes all the features, structures, configurations, and functionality of the first inflatable member 2502 and is a mirror image of the first inflatable member 2502. For example, in various embodiments, the second inflatable member 2512 can have at least one baffle to support a shape of the second inflatable member when the second inflatable member is inflated. In the embodiment shown in FIG. 25B, the neck member 2503 includes a total of eight baffles 2508-1 to 2508-8. In various embodiments, neck member 2503 can be formed to include any number of baffles.

Similar to the embodiment illustrated in FIG. 25A, the second inflatable member, illustrated in FIG. 25B, can include a surface defining at least one opening in fluid communication with a source of thermally treated air. As shown in FIG. 25B, surface 2507 includes an arcuate shape and defines three openings 2510-4 to 2506-6. In various embodiments, the openings 2510-1 to 2510-3 of first inflatable member 2502 and openings to 25104 to 2510-6 of second inflatable member 2512 can be positioned such that they are spaced equally apart or they can be positioned such that they are spaced at varying distances from each other. In various embodiments, the openings 2510-1 to 2510-6 can be positioned to direct air (indicated by arrows 2530 in FIG. 25E) radially around and on the patient's neck. The second inflatable member 2512 can be configured to facilitate a flow of thermally treated air (e.g., cooled air) through the second inflatable member 2512 and out the three openings 25104 to 2510-6 in the same or similar manner as the first inflatable member 2502.

In various embodiments, the surfaces of the first and second inflatable member defining the number of openings also define a cover when reversibly coupled or linked. In such embodiments, when the neck member is positioned over a patient's neck area, the cover of the neck member is spaced apart from and around a portion of the neck area of the patient. For example, in various embodiments, the surfaces 2506 defining the at least one opening 2510 of both the first inflatable member 2502 and the second inflatable member 2512 can each include an arcuate shape that, when linked together, form a cover 2524 having an arch shape, as shown in FIG. 25B. As discussed herein, the cover 2524 can be spaced apart from and around a portion of the neck area of the patient when the first inflatable member 2502 is linked to the second inflatable member 2512. In various embodiments, surfaces defining the number of openings can include other shapes, for example, planar shapes, such that when the surfaces are reversibly coupled or linked, the cover forms a polygonal shape, such as a semi-square shape, as shown, in FIG. 25D. Other shapes for the cover are also contemplated, and can include, but are not limited to, semi-hexagonal shapes, octagonal shapes, and shapes having a combination of arcuate and multilateral or polygonal surfaces.

The neck member 2503 can include a neck member connector 2518 configured to link a first end 2520 of the first inflatable member 2502 to a first end 2522 of the second inflatable member 2512. In various embodiments, the first ends 2520 and 2520 of the first and second inflatable members 2502 and 2512 can be positioned proximal a laryngeal prominence of a patient when the first and second inflatable members 2502 and 2512 are linked. Neck member connector 2518 provides stability and control to the neck member 2503 when the first and second inflatable members are linked during operation of the neck member (i.e., when air is flowing through the neck member). Unlinking the first and second inflatable members by detaching the neck member connector 2518 from the first and/or second inflatable member 2502 and 2512 allows the members to be pulled away from each other along their pivot points, as discussed herein, and thus provides for proper positioning of the patient's head. Once the patient's head is properly positioned, the first and second inflatable member 2502 and 2512 can be linked using the neck member connector 2518. In various embodiments, the neck member connector 2518 can be formed of a number of materials, components, etc, that include, but are not limited to, a hook and loop material, clamps, hooks, and buttons, among others.

Similar to the embodiment illustrated in FIG. 25A, the first and second inflatable members 2502 and 2512 can each include an air inlet 2512 for providing the thermally treated air (e.g. warmed or cooled air) to the first and second inflatable members 2502 and 2512.

Figure 25D:
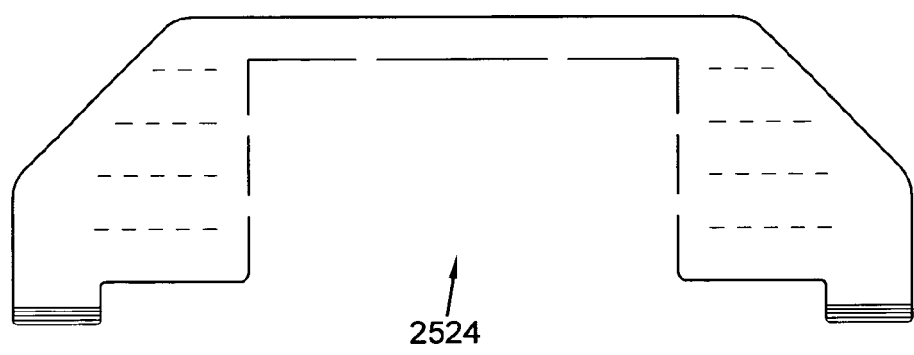
FIG. 25D illustrates another embodiment of a neck member of the present disclosure.
Figure 25E:
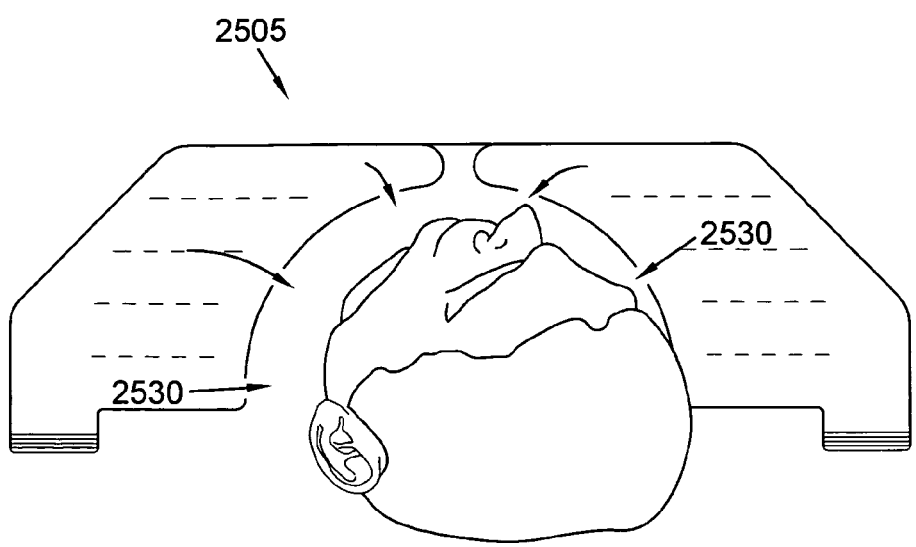
FIG. 25E illustrates an embodiment of a neck member in operation on a patient.

FIG. 25D illustrates another embodiment of a neck member 2505 of the present disclosure. As shown in FIG. 25D, neck member 2503 can include all or some of the features, structures, configurations, and functionality of neck member 2501 and 2503. For example, neck member 25D can be inflatable and can include at least one baffle 2508, an air inlet 2512, at least one opening 2510, and an arcuate surface 2506 defining a cover 2524. In the embodiment shown in FIG. 25D, neck member 2505 does not include a connector, such as neck member connector 2518 illustrated in FIG. 25B. In this embodiment, the air inlets 2512 can provide thermally treated air to the neck member 2505 and each can function as a pivot point. As discussed herein, the pivoting of the neck member allows an operator of the first inflatable member to move the neck member to position a patient and for patient exit from the patient support surface.

As discussed herein, in various embodiments of FIGS. 25A to 25E, neck members 2501, 2503, and 2505 each include one or more inflatable members, for example, first inflatable member 2502 in FIG. 25A and first and second inflatable members 2502 and 2512 of FIG. 25B. In some embodiments of FIGS. 25A to 25E, the neck members 2501, 2503, and 2505, can be non-inflatable. In such embodiments, the neck members can be formed of a rigid or semi-rigid material such as foam that provides structural support to the neck members 2501, 2503, and 2505. In order to direct air to the patient's neck area, the openings defined by the surfaces of the neck members can be in fluid communication with one or more conduits (not shown) that extend from the openings through the foam or other rigid or semi-rigid material and to the air inlets. In this manner, the conduits can facilitate the transfer of cooled air from a source of thermally treated air through the neck members and out the openings.

Figure 26A:
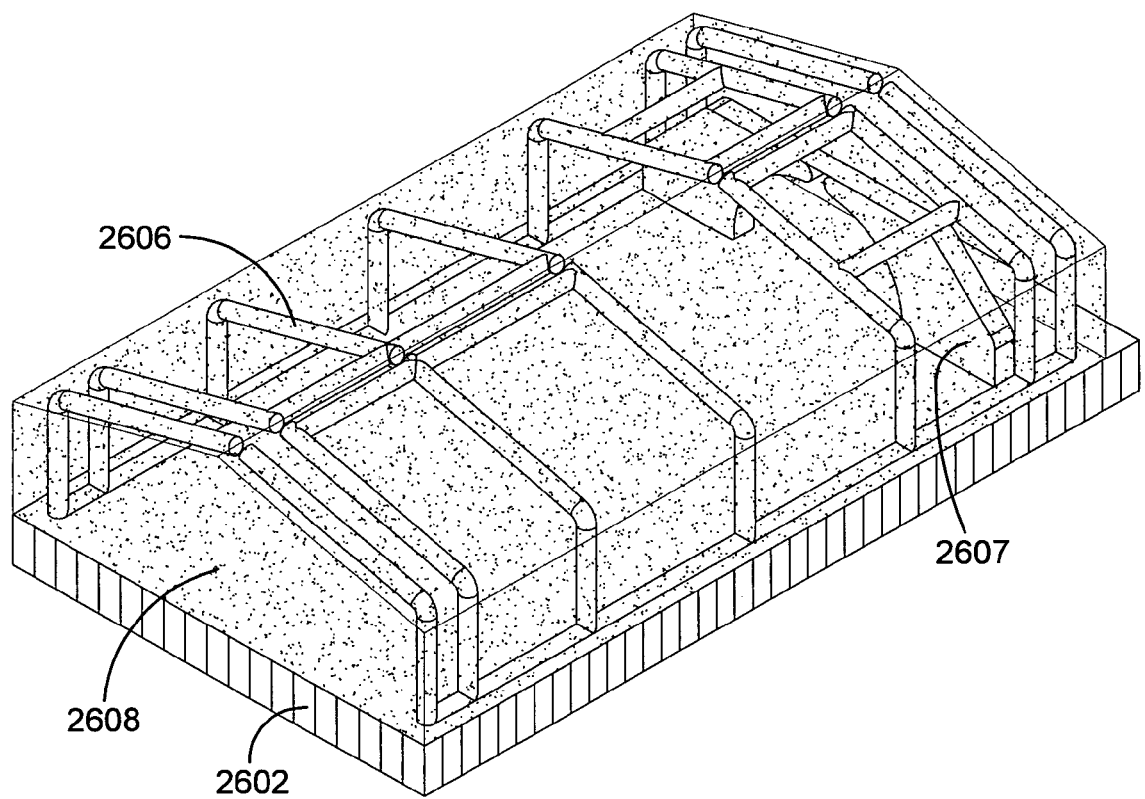
FIGS. 26A and 26B illustrate an embodiment of a system of the present disclosure.
Figure 26B:
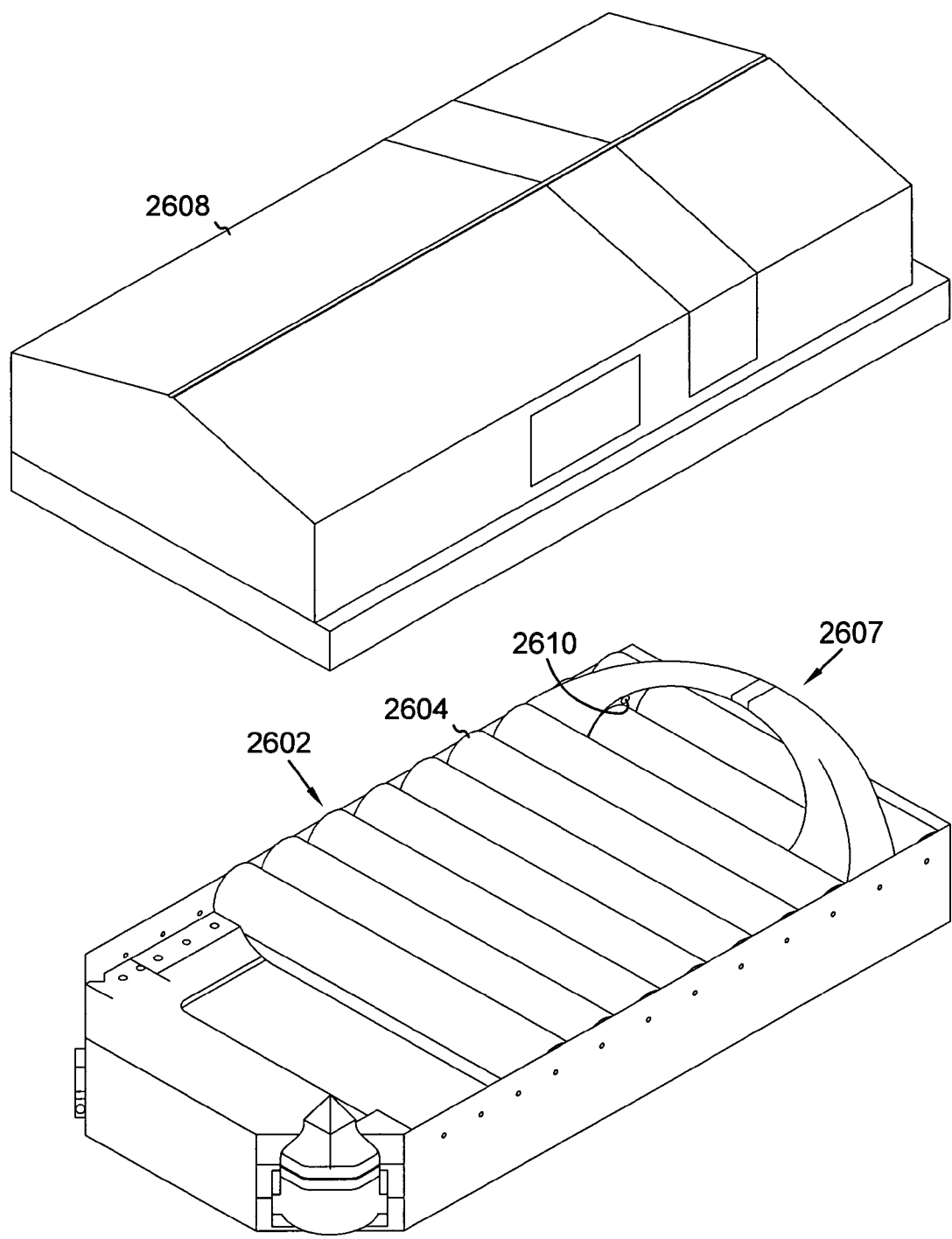

FIGS. 26A and 26B illustrate various embodiments of a system 2600 of the present disclosure. In the embodiments illustrated in FIGS. 26A and 26B, various components are provided that facilitate the circulation of air within the system 2600 to provide thermal control to a patient such as cooling a patient to a temperature below normal body temperature. In various embodiments, the system 2600 can include a patient support surface 2602. The patient support surface provided to the system can include a variety of shapes, sizes, and materials. For example, in some embodiments, the patient support surface 2602 can include a number of inflatable air cells 2604 and 1307 that extend transversely across the patient support surface, as provided in FIG. 26B and in FIGS. 13A-13C respectively.

System 2600 can include a framework of inflatable tubes 2606 mounted on the patient support surface 2602. In various embodiments, the framework of inflatable tubes can be the same or similar to the tubular support framework 200 as illustrated in FIG. 7. In various embodiments, mounting the framework of inflatable tubes on the patient support surface can include coupling various portions of the framework of inflatable tubes to other components of the system, for example, coupling the framework of inflatable tubes to the patient support surface, a manifold system, or various valves, as described herein. In some embodiments mounting the framework of inflatable tubes on the patient support surface can include positioning the framework on a surface of the patient support surface.

The system 2600 can also include an air tent 2608 mounted on the framework of inflatable tubes 2606, as shown, for example, in FIG. 26A. In various embodiments, the air tent 2608 can be positioned on the patient support surface, as shown, for example, in FIGS. 26A and 26B. The air tent 2608 can include a number of different configurations. For example, the air tent 2608 can be the same or similar to air tent 2 illustrated in FIGS. 3A-5A, air tent 100 in FIG. 6, air tent 300 in FIG. 9, or air tent 1312 in FIG. 13C.

In various embodiments, system 2600 includes a source of thermally treated air, such as cool or warm air, (not shown in FIGS. 26A and 26B) in fluid communication with the patient support surface 2602. In some embodiments, temperature of the patient can be measured and can be used to adjust the thermal properties of the air. The source of thermally treated air can include, for example, thermal control unit (TCU) 1802 illustrated in FIG. 18 or thermal control unit 2002 illustrated in FIG. 20. The source of thermally treated air can be in fluid communication with the patient support surface 2602, the framework of inflatable tubes 2606, and an interior of the air tent.

The system 2600 also includes a flow system (shown as 1800 in FIG. 18). As discussed herein, the flow system includes the TCU, a manifold system, and other components. In such embodiments, the TCU of the flow system can distribute pressurized, thermally controlled air through the manifold system to the patient support surface, an inflatable portion of the air tent, and into an enclosed area defined by the air tent above the inflatable support surface, as discussed herein. In some embodiments, air is re-circulated through the manifold system from the patient support surface, the inflatable portion of the air tent, and the enclosed area to conserve energy.

In various embodiments of system 2600, the manifold system can be positioned within the patient support surface to distribute air to the patient support surface 2602, the framework of inflatable tube 2608, the interior of the air tent, and a neck member 2607, as will be discussed herein. The flow system provides the capability for the air tent, when inflated, supports the air tent above the patient, and when deflated, falls away from the patient.

System 2600 also includes a neck member 2607. In various embodiments, the neck member 2607 can be coupled to the patient support surface 2602 and/or various components described herein. As discussed herein, neck member can include a surface that defines at least one opening 2610, as shown, for example, in FIG. 26B. In various embodiments neck member 2607 can be any one of the neck members described and illustrated herein, for example, neck member 2501 in FIG. 25A, neck member 2503 in FIG. 25B, or neck member 2505 in FIG. 25C.

While the present disclosure has been shown and described in detail above, it will be clear to the person skilled in the art that changes and modifications may be made without departing from the scope of the invention. As such, that which is set forth in the foregoing description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the invention described herein can be included within the scope of the present disclosure.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claims standing on its own as a separate embodiment.

What is claimed is:

1. A method to circulate air within a patient cooling system comprising:
   providing an inflatable patient support surface having a manifold system positioned within the inflatable patient support surface;
   mounting an air tent to the inflatable patient support surface;
   coupling a neck member to the patient support surface wherein the neck member is configured to extend around a user's neck;
   providing pressurized, thermally treated air into the manifold system; and
   distributing the pressurized, thermally controlled air through the manifold system to the inflatable patient support surface, an inflatable portion of the air tent, and into the enclosed area defined by the air tent above the inflatable patient support surface.

2. The method of claim 1, including recirculating the air through the manifold system from the patient support surface, the inflatable portion of the air tent, and the enclosed area to conserve energy.

3. The method of claim 1, including measuring the temperature of the patient for adjustment of the thermal properties of the air.

* * * * *